(12) United States Patent
Takenouchi

(10) Patent No.: US 12,373,973 B2
(45) Date of Patent: Jul. 29, 2025

(54) MEDICAL IMAGE PROCESSING APPARATUS, ENDOSCOPE SYSTEM, MEDICAL IMAGE PROCESSING METHOD, AND PROGRAM

(71) Applicant: FUJIFILM Corporation, Tokyo (JP)

(72) Inventor: Seiya Takenouchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 342 days.

(21) Appl. No.: 17/878,033

(22) Filed: Jul. 31, 2022

(65) Prior Publication Data

US 2022/0383533 A1    Dec. 1, 2022

Related U.S. Application Data

(63) Continuation of application No. PCT/JP2021/003330, filed on Jan. 29, 2021.

(30) Foreign Application Priority Data

Feb. 6, 2020 (JP) ................................. 2020-018886

(51) Int. Cl.
*G06T 7/62* (2017.01)
*G06T 7/00* (2017.01)

(52) U.S. Cl.
CPC .............. *G06T 7/62* (2017.01); *G06T 7/0016* (2013.01); *G06T 2207/10068* (2013.01); *G06T 2207/30096* (2013.01)

(58) Field of Classification Search
CPC ...................... G06T 7/62; G06T 7/0016; G06T 2207/10068; G06T 2207/30096
See application file for complete search history.

(56) References Cited

U.S. PATENT DOCUMENTS 8,744,133 B1 * 6/2014 Troy .................. G06T 7/001
                                            382/106
10,799,098 B2    10/2020 Oosake
(Continued)

FOREIGN PATENT DOCUMENTS

CN    110663251    1/2020
JP    2010512173   4/2010
(Continued)

OTHER PUBLICATIONS

"International Search Report (Form PCT/ISA/210) of PCT/JP2021/003330," mailed on Apr. 6, 2021, with English translation thereof, pp. 1-5.

(Continued)

*Primary Examiner* — Kevin Ky
(74) *Attorney, Agent, or Firm* — JCIPRNET

(57) ABSTRACT

An object of the present invention is to provide a medical image processing apparatus, an endoscope system, a medical image processing method, and a program that assist a user in estimating an accurate size of a region of interest. A medical image processing apparatus according to an aspect of the present invention is a medical image processing apparatus including a processor. The processor is configured to acquire images in time-series, make a determination of whether a region of interest in each of the images is suitable for size estimation, and report, by using a reporting device, a result of the determination and operation assistance information for improving the result of the determination.

20 Claims, 16 Drawing Sheets

(56) References Cited

U.S. PATENT DOCUMENTS

| | | | |
|---|---|---|---|
| 11,244,195 B2* | 2/2022 | Pao | G06V 10/7747 |
| 12,080,388 B1* | 9/2024 | Tal | G06F 16/93 |
| 2002/0191074 A1 | 12/2002 | Ogawa | |
| 2008/0058593 A1 | 3/2008 | Gu et al. | |
| 2009/0041325 A1* | 2/2009 | Luo | G06T 7/0012 |
| | | | 382/128 |
| 2011/0021874 A1* | 1/2011 | Ogawa | G02B 23/2484 |
| | | | 600/109 |
| 2013/0141722 A1* | 6/2013 | Wood | G01N 21/53 |
| | | | 356/338 |
| 2014/0232743 A1* | 8/2014 | Na | H04N 1/32144 |
| | | | 345/629 |
| 2015/0339833 A1* | 11/2015 | Harada | H04N 13/275 |
| | | | 348/135 |
| 2015/0356754 A1* | 12/2015 | Kaftan | G06T 5/73 |
| | | | 382/131 |
| 2016/0078614 A1* | 3/2016 | Ryu | G06T 7/12 |
| | | | 382/128 |
| 2017/0266438 A1* | 9/2017 | Sano | A61N 1/40 |
| 2019/0029749 A1* | 1/2019 | Garcia | A61B 34/10 |
| 2019/0089910 A1* | 3/2019 | Banik | G06T 5/77 |
| 2019/0311476 A1 | 10/2019 | Hayami et al. | |
| 2020/0305840 A1* | 10/2020 | Sboros | G06T 7/73 |
| 2021/0044750 A1 | 2/2021 | Kamon | |
| 2021/0298984 A1* | 9/2021 | Bulea | A61H 3/00 |
| 2022/0383533 A1* | 12/2022 | Takenouchi | A61B 1/0005 |
| 2024/0270113 A1* | 8/2024 | Anand | B60L 53/665 |

FOREIGN PATENT DOCUMENTS

| | | |
|---|---|---|
| JP | 4515081 | 7/2010 |
| WO | 2018105063 | 6/2018 |
| WO | 2019082993 | 5/2019 |
| WO | 2019146077 | 8/2019 |
| WO | 2019220859 | 11/2019 |

OTHER PUBLICATIONS

"Written Opinion of the International Searching Authority (Form PCT/ISA/237) of PCT/JP2021/003330," mailed on Apr. 6, 2021, with English translation thereof, pp. 1-6.

"Search Report of Europe Counterpart Application", issued on Jun. 30, 2023, p. 1-p. 8.

"Office Action of China Counterpart Application", issued on Sep. 30, 2024, with English translation thereof, p. 1-p. 19.

* cited by examiner

※ a:b IS ANY RATIO

MEDICAL IMAGE PROCESSING APPARATUS, ENDOSCOPE SYSTEM, MEDICAL IMAGE PROCESSING METHOD, AND PROGRAM

CROSS-REFERENCE TO RELATED APPLICATIONS

The present application is a Continuation of PCT International Application No. PCT/JP2021/003330 filed on Jan. 29, 2021 claiming priority under 35 U.S.C § 119(a) to Japanese Patent Application No. 2020-018886 filed on Feb. 6, 2020. Each of the above applications is hereby expressly incorporated by reference, in its entirety, into the present application.

BACKGROUND OF THE INVENTION

1. Field of the Invention

The present invention relates to a medical image processing apparatus, an endoscope system, a medical image processing method, and a program.

2. Description of the Related Art

In the field of examinations and diagnoses using medical images, a system for assisting a user in more efficiently conducting an examination or the like is expected. For example, JP2010-512173A describes discarding a low-quality image frame and providing a satisfactory image from video data, thereby standardizing the detection or analysis of a polyp or the like.

SUMMARY OF THE INVENTION

In the above-described assistance for a user, assistance in estimating the size of a target object (a region of interest) such as a lesion can be used for determining whether to excise a lesion, reducing labor for creating a post-operative report, or the like. However, an issue of image distortion resulting from, for example, an optical system, may arise depending on an apparatus that uses a medical image, such as an endoscope, and it may be impossible to appropriately image a target object due to difficulty in operating an apparatus such as a scope. Thus, it may be difficult to accurately estimate the size of the target object, and it may be impossible to provide an estimation result with consistency.

In addition, although an examination, diagnosis, and treatment can be simultaneously performed using an endoscope, blindly treating a portion considered as a lesion imposes a large burden on both a user and a patient. Thus, the size of a lesion is adopted as an indicator for treatment. On the basis of this, the user determines whether to excise the lesion, which forceps to use, and so forth. This is because the possibility of canceration increases as the size of a lesion increases. However, it is usually difficult to accurately and immediately measure the size of a lesion. This is because size measurement is greatly affected by the difficulty of scope operation, the aberration of a lens, a change in the shape (expansion or contraction) of the large intestine, or the like. In endoscopy in which all of an examination, a diagnosis, and a treatment have to be performed in real time, a highly advanced skill and concentration are required.

However, the related art such as JP2010-512173A does not take such circumstances into consideration.

The present invention has been made in view of these circumstances, and an object of the present invention is to provide a medical image processing apparatus, an endoscope system, a medical image processing method, and a program that assist a user in estimating an accurate size of a region of interest.

A medical image processing apparatus according to a first aspect of the present invention is a medical image processing apparatus including a processor. The processor is configured to acquire images in time series, make a determination of whether a region of interest in each of the images is suitable for size estimation, and report, by using a reporting device, a result of the determination and operation assistance information for improving the result of the determination. In the first aspect, it is determined whether a region of interest (target object) is suitable for size estimation, and a result of the determination and operation assistance information for improving the result of the determination are reported by the reporting device. Accordingly, a user performs an operation according to the operation assistance information to improve the result of the determination. This makes it possible to assist the user in estimating an accurate size of the region of interest.

In a medical image processing apparatus according to a second aspect, in the first aspect, the processor is configured to calculate, by image processing, an accuracy of the size estimation and compare the accuracy with a predetermined threshold value, thereby determining whether the region of interest is suitable for the size estimation.

In a medical image processing apparatus according to a third aspect, in the second aspect, the processor is configured to report the accuracy by using the reporting device.

In a medical image processing apparatus according to a fourth aspect, in the second or third aspect, the processor is configured to calculate the accuracy by using a clarity of a region including the region of interest.

In a medical image processing apparatus according to a fifth aspect, in any one of the second to fourth aspects, the processor is configured to calculate the accuracy in accordance with a distance between a reference position and the region of interest in the acquired images. The reference position may be, for example, the center of the images.

In a medical image processing apparatus according to a sixth aspect, in any one of the second to fifth aspects, the processor is configured to calculate the accuracy in accordance with an imaging angle for imaging the region of interest.

In a medical image processing apparatus according to a seventh aspect, in any one of the first to sixth aspects, the medical image processing apparatus includes a storage device configured to store one or more reference images each indicating an imaging state suitable for the size estimation. The processor is configured to cause the reporting device to display at least one of the one or more reference images.

In a medical image processing apparatus according to an eighth aspect, in any one of the first to seventh aspects, the processor is configured to cause the reporting device to display the result of the determination and the operation assistance information in a first region in the acquired images and/or a second region that does not overlap the acquired images.

In a medical image processing apparatus according to a ninth aspect, in any one of the first to eighth aspects, the processor is configured to determine, in an image having two or more regions of interest, one target on which the size estimation is to be performed.

In a medical image processing apparatus according to a tenth aspect, in the ninth aspect, the processor is configured to determine, as the target, a region of interest having a largest area of the two or more regions of interest.

In a medical image processing apparatus according to an eleventh aspect, in the ninth aspect, the processor is configured to determine, as the target, a region of interest having a highest accuracy of the size estimation of the two or more regions of interest.

In a medical image processing apparatus according to a twelfth aspect, in any one of the first to eleventh aspects, the processor is configured to perform the size estimation on the region of interest, and report, by using the reporting device, a result of the estimation.

In a medical image processing apparatus according to a thirteenth aspect, in any one of the first to twelfth aspects, the processor is configured to recognize a user operation, make a determination of whether the recognized user operation follows the operation assistance information, and report, by using the reporting device, a result of the determination.

An endoscope system according to a fourteenth aspect of the present invention includes the medical image processing apparatus according to any one of the first to thirteenth aspects, the reporting device, and an endoscope configured to be inserted into a subject as a photographic subject and capture medical images. The processor is configured to acquire the images captured by the endoscope. The endoscope system according to the fourteenth aspect includes the medical image processing apparatus according to any one of the first to thirteenth aspects and is thus capable of assisting a user in estimating an accurate size of a region of interest.

In an endoscope system according to a fifteenth aspect, in the fourteenth aspect, the reporting device includes a display configured to perform screen display of information and/or a speaker configured to output a sound, and the processor is configured to report, by using the display and/or the speaker, the result of the determination and the operation assistance information with use of at least one of a figure, text, or a sound.

In an endoscope system according to a sixteenth aspect, in the fourteenth or fifteenth aspect, the operation assistance information includes at least one of first information indicating a direction in which the endoscope is to be moved and/or an amount by which the endoscope is to be moved, second information indicating ON/OFF of air supply from the endoscope and/or ON/OFF of water supply from the endoscope, third information indicating ON/OFF of illumination from the endoscope and/or a degree of the illumination, fourth information indicating ON/OFF of image processing on the acquired images and/or a degree of the image processing, or fifth information indicating whether a treatment tool is to be used.

In an endoscope system according to a seventeenth aspect, in any one of the fourteenth to sixteenth aspects, the processor is configured to acquire individual information of the endoscope, and perform the determination and/or the reporting on the basis of the individual information.

A medical image processing method according to an eighteenth aspect of the present invention includes an image acquisition step of acquiring images in time-series, an estimation state determination step of making a determination of whether a region of interest in each of the images is suitable for size estimation, and a reporting step of reporting, by using a reporting device, a result of the determination and operation assistance information for improving the result of the determination.

In the medical image processing method according to the eighteenth aspect, it is possible to assist a user in estimating an accurate size of a region of interest, as in the first aspect. The medical image processing method according to the eighteenth aspect may further include configurations similar to those of the second to thirteenth aspects (steps corresponding to functions performed by the processor). In addition, the medical image processing methods of these aspects may be regarded as methods for operating the medical image processing apparatus including the processor.

A program according to a nineteenth aspect causes a computer to execute the medical image processing method according to the eighteenth aspect. In addition, a non-transitory recording medium storing a computer-readable code of the program according to the nineteenth aspect may be included in an aspect of the present invention.

DESCRIPTION OF THE PREFERRED EMBODIMENTS

Hereinafter, an embodiment of a medical image processing apparatus, an endoscope system, a medical image processing method, and a program according to the present invention will be described in detail with reference to the accompanying drawings.

First Embodiment

Configuration of Endoscope System

Figure 1:
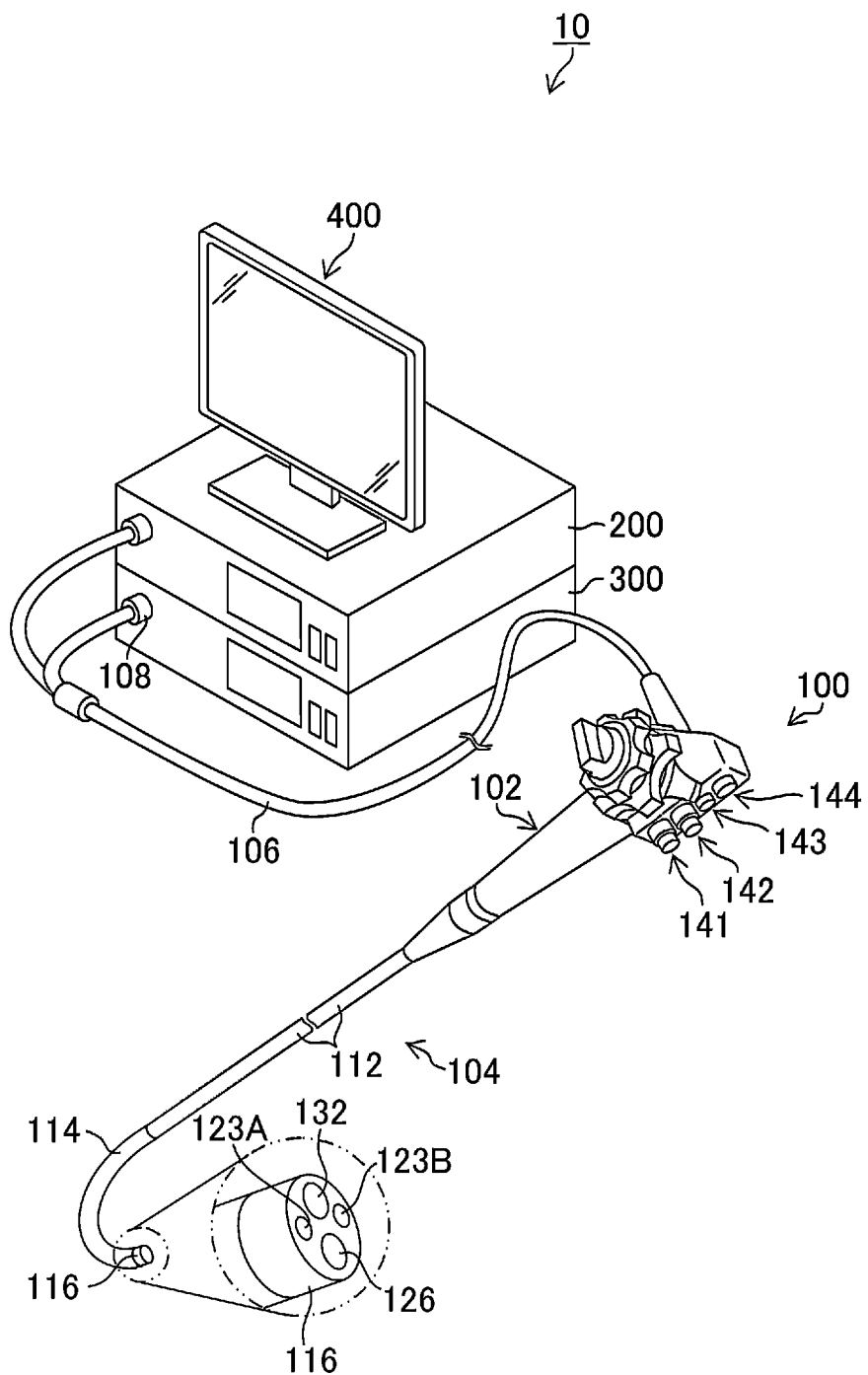
FIG. 1 is a diagram illustrating the configuration of an endoscope system according to a first embodiment.
Figure 2:
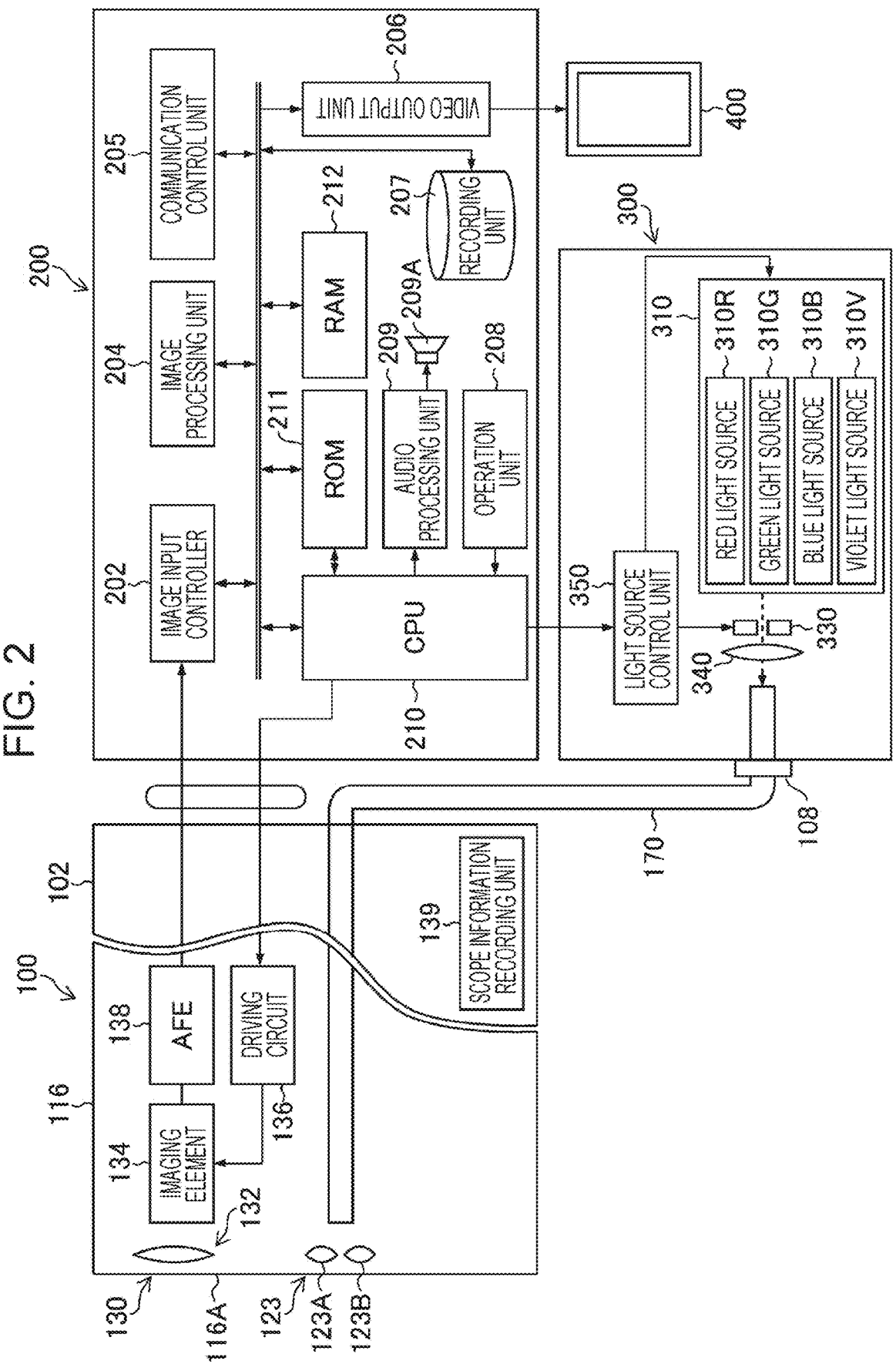
FIG. 2 is another diagram illustrating the configuration of the endoscope system.

FIG. 1 is an external appearance diagram of an endoscope system 10 (an endoscope system, a medical image processing apparatus), and FIG. 2 is a block diagram illustrating the configuration of a main part of the endoscope system 10. As illustrated in FIGS. 1 and 2, the endoscope system 10 is constituted by an endoscope 100 (an image acquiring unit, an endoscope), a processor 200 (a medical image processing apparatus, a processor, an image acquiring unit, a size estimating unit, an estimation state determining unit, a reporting control unit, a scope information acquiring unit, an operation recognizing unit, a recording control unit, a display control unit), a light source apparatus 300 (a light source apparatus), and a monitor 400 (a display device, a reporting device, a display).

Configuration of Endoscope

The endoscope 100 includes a handheld operation section 102 and an insertion section 104 that communicates with the handheld operation section 102. An operator (a user) operates the handheld operation section 102 while grasping it and inserts the insertion section 104 into a body of a subject (a living body) to perform observation. The handheld operation section 102 is provided with an air/water supply button 141, a suction button 142, a function button 143 to which various functions are allocated, and an imaging button 144 for receiving an imaging instruction operation (a still image, a moving image).

The handheld operation section 102 is provided with a scope information recording unit 139 that stores individual information (individual information, scope information) of the endoscope 100. The individual information includes, for example, the type (direct view, side view, or the like), model, individual identification number, optical system characteristics (viewing angle, distortion, and so forth), and so forth of the endoscope 100. A scope information acquiring unit 230 (a scope information acquiring unit, an individual information acquiring unit; see FIG. 3) acquires the individual information, and the individual information is used for processing by an estimation state determining unit 226 and a reporting control unit 228. The scope information recording unit 139 may be provided in a light guide connector 108.

The insertion section 104 is constituted by a soft part 112, a bending part 114, and a tip rigid part 116, which are arranged in this order from the handheld operation section 102 side. That is, the bending part 114 is connected to a base end side of the tip rigid part 116, and the soft part 112 is connected to a base end side of the bending part 114. The handheld operation section 102 is connected to a base end side of the insertion section 104. The user is able to change the orientation of the tip rigid part 116 in an up, down, left, or right direction by causing the bending part 114 to bend by operating the handheld operation section 102. The tip rigid part 116 is provided with an imaging optical system 130, an illumination unit 123, a forceps port 126, and so forth (see FIGS. 1 and 2).

During observation or treatment, an operation of an operation unit 208 (see FIG. 2) enables white light and/or narrow-band light (one or more of red narrow-band light, green narrow-band light, blue narrow-band light, and violet narrow-band light) to be radiated from illumination lenses 123A and 123B of the illumination unit 123. In addition, an operation of the air/water supply button 141 enables washing water to be ejected from a water supply nozzle that is not illustrated, so that an imaging lens 132 (an imaging lens, an imaging unit) of the imaging optical system 130 and the illumination lenses 123A and 123B can be washed. The forceps port 126 opening in the tip rigid part 116 communicates with a pipe line that is not illustrated, so that a treatment tool that is not illustrated and is for extirpating a tumor or the like can be inserted into the pipe line and necessary treatment can be given to a subject by moving the treatment tool forward or backward as appropriate.

As illustrated in FIGS. 1 and 2, the imaging lens 132 (an image acquiring unit) is disposed on a distal-end-side surface 116A of the tip rigid part 116. An imaging element 134 (an imaging element, an image acquiring unit) of a complementary metal-oxide semiconductor (CMOS) type, a driving circuit 136 (an image acquiring unit), and an analog front end (AFE) 138 (an image acquiring unit) are disposed behind the imaging lens 132, and these elements output an image signal. The imaging element 134 is a color imaging element and includes a plurality of pixels constituted by a plurality of light-receiving elements arranged in a matrix (arranged two-dimensionally) in a specific pattern arrangement (Bayer arrangement, X-Trans (registered trademark) arrangement, honeycomb arrangement, or the like). Each pixel of the imaging element 134 includes a microlens, a red (R), green (G), or blue (B) color filter, and a photoelectric conversion unit (a photodiode or the like). The imaging optical system 130 is capable of generating a color image from pixel signals of three colors, red, green, and blue, and is also capable of generating an image from pixel signals of any one or two colors among red, green, and blue. The imaging element 134 may be of a charge coupled device (CCD) type. Each pixel of the imaging element 134 may further include a violet color filter corresponding to a violet light source 310V and/or an infrared filter corresponding to an infrared light source.

An optical image of a subject is formed on a light-receiving surface (an imaging surface) of the imaging element 134 by the imaging lens 132, converted into an electric signal, output to the processor 200 through a signal cable that is not illustrated, and converted into a video signal. Accordingly, an endoscopic image (an image, a medical image) of the photographic subject is displayed on the monitor 400, which is connected to the processor 200.

The illumination lenses 123A and 123B of the illumination unit 123 are provided next to the imaging lens 132 on the distal-end-side surface 116A of the tip rigid part 116. An emission end of a light guide 170, which will be described below, is disposed behind the illumination lenses 123A and 123B. The light guide 170 extends through the insertion section 104, the handheld operation section 102, and a universal cable 106, and an incidence end of the light guide 170 is located in the light guide connector 108.

A user performs imaging (under control of an image acquiring unit 220) at a determined frame rate while inserting or removing the endoscope 100 (the insertion section 104) having the above-described configuration into or from a living body as a subject, thereby being capable of sequentially capturing images (time-series images) of the inside of the living body, in time series.

Configuration of Light Source Apparatus

As illustrated in FIG. 2, the light source apparatus 300 is constituted by a light source 310 for illumination, a diaphragm 330, a condenser lens 340, a light source control unit 350, and so forth, and causes observation light to enter the light guide 170. The light source 310 includes a red light source 310R, a green light source 310G, a blue light source 310B, and a violet light source 310V that radiate red narrow-band light, green narrow-band light, blue narrow-band light, and violet narrow-band light, respectively, and is capable of radiating red narrow-band light, green narrow-band light, blue narrow-band light, and violet narrow-band light. The illuminance of observation light from the light source 310 is controlled by the light source control unit 350, which is capable of changing (increasing or decreasing) the illuminance of observation light or stopping illumination as necessary.

The light source 310 is capable of emitting red narrow-band light, green narrow-band light, blue narrow-band light, and violet narrow-band light in any combination. For example, the light source 310 is capable of simultaneously emitting red narrow-band light, green narrow-band light, blue narrow-band light, and violet narrow-band light to radiate white light (normal light) as observation light, and is also capable of emitting any one or two of red narrow-band light, green narrow-band light, blue narrow-band light, and violet narrow-band light to radiate narrow-band light (special light). The light source 310 may further include an infrared light source that radiates infrared light (an example of narrow-band light). Alternatively, with use of a light source that radiates white light and a filter that allows white light and each narrow-band light to pass therethrough, white light or narrow-band light may be radiated as observation light.

Wavelength Range of Light Source

The light source 310 may be a light source that generates light in a white range or light in a plurality of wavelength ranges as the light in the white range, or may be a light source that generates light in a specific wavelength range narrower than the white wavelength range. The specific wavelength range may be a blue range or green range in a visible range, or may be a red range in the visible range. In a case where the specific wavelength range is the blue range or green range in the visible range, the specific wavelength range may include a wavelength range of 390 nm or more and 450 nm or less or a wavelength range of 530 nm or more and 550 nm or less, and the light in the specific wavelength range may have a peak wavelength in the wavelength range of 390 nm or more and 450 nm or less or the wavelength range of 530 nm or more and 550 nm or less. In a case where the specific wavelength range is the red range in the visible range, the specific wavelength range may include a wavelength range of 585 nm or more and 615 nm or less or a wavelength range of 610 nm or more and 730 nm or less, and the light in the specific wavelength range may have a peak wavelength in the wavelength range of 585 nm or more and 615 nm or less or the wavelength range of 610 nm or more and 730 nm or less.

The above-described specific wavelength range may include a wavelength range in which a light absorption coefficient is different between oxyhemoglobin and deoxyhemoglobin, and the above-described light in the specific wavelength range may have a peak wavelength in the wavelength range in which the light absorption coefficient is different between oxyhemoglobin and deoxyhemoglobin. In this case, the specific wavelength range may include a wavelength range of 400±10 nm, a wavelength range of 440±10 nm, a wavelength range of 470±10 nm, or a wavelength range of 600 nm or more and 750 nm or less, and may have a peak wavelength in the wavelength range of 400±10 nm, the wavelength range of 440±10 nm, the wavelength range of 470±10 nm, or the wavelength range of 600 nm or more and 750 nm or less.

The wavelength range of the light generated by the light source 310 may include a wavelength range of 790 nm or more and 820 nm or less or a wavelength range of 905 nm or more and 970 nm or less, and the light generated by the light source 310 may have a peak wavelength in the wavelength range of 790 nm or more and 820 nm or less or the wavelength range of 905 nm or more and 970 nm or less.

Alternatively, the light source 310 may include a light source that radiates excitation light whose peak is 390 nm or more and 470 nm or less. In this case, a medical image (an inside-of-living-body image) having information about fluorescence emitted by a fluorescent substance in a subject (a living body) can be acquired. In the case of acquiring a fluorescence image, a pigment for a fluorescence method (fluorescein, acridine orange, or the like) may be used.

It is preferable that the type of the light source 310 (a laser light source, a xenon light source, a light-emitting diode (LED) light source, or the like), the wavelength of the light source 310, the presence or absence of a filter for the light source 310, and so forth be determined in accordance with the type, area, purpose of observation, or the like of a photographic subject. It is also preferable that, during observation, the wavelengths of observation light be combined and/or switched in accordance with the type, area, purpose of observation, or the like of a photographic subject. In the case of switching the wavelength, for example, a disc-shaped filter (a rotary color filter) that is disposed in front of the light source and that is provided with a filter for transmitting or blocking light of a specific wavelength may be rotated to switch the wavelength of light to be radiated.

The imaging element used to carry out the present invention is not limited to a color imaging element in which color filters are disposed for the individual pixels, such as the imaging element 134, and may be a monochrome imaging element. In the case of using a monochrome imaging element, imaging can be performed in a frame sequential (color sequential) manner by sequentially switching the wavelength of observation light. For example, the wavelength of outgoing observation light may be sequentially switched among violet, blue, green, and red, or wide-band light (white light) may be radiated and the wavelength of outgoing observation light may be switched by using a rotary color filter (red, green, blue, violet, and the like). Alternatively, one or a plurality of types of narrow-band light (green, blue, violet, and the like) may be radiated and the wavelength of outgoing observation light may be switched by using a rotary color filter (green, blue, violet, and the like). The narrow-band light may be infrared light of two or more different wavelengths (first narrow-band light and second narrow-band light).

As a result of connecting the light guide connector 108 (see FIGS. 1 and 2) to the light source apparatus 300, observation light radiated by the light source apparatus 300 is transmitted through the light guide 170 to the illumination lenses 123A and 123B and is radiated from the illumination lenses 123A and 123B to an observation range.

Configuration of Processor

The configuration of the processor 200 will be described with reference to FIG. 2. In the processor 200, an image input controller 202 receives an image signal output from the endoscope 100, an image processing unit 204 (a medical image processing unit, a processor) performs necessary image processing thereon, and a video output unit 206 outputs a resulting image signal. Accordingly, an observation image (an inside-of-living-body image) is displayed on the monitor 400 (a display device). These processing operations are performed under control by a central processing unit (CPU) 210 (a processor). A communication control unit 205 controls communication, for acquiring a medical image, with a hospital information system (HIS), a hospital local area network (LAN), and/or an external system or network that are not illustrated.

Functions of Image Processing Unit

Figure 3:
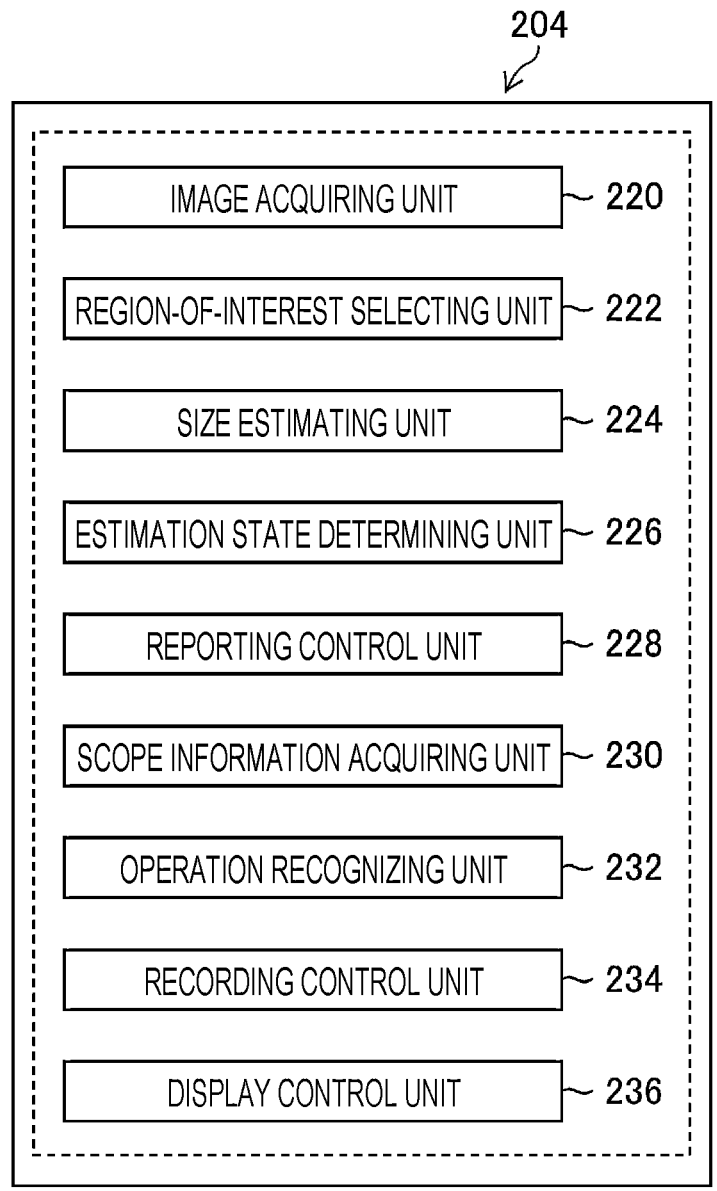
FIG. 3 is a functional block diagram of an image processing unit.

FIG. 3 is a functional block diagram of the image processing unit 204. The image processing unit 204 includes the image acquiring unit 220 (an image acquiring unit, a medical image acquiring unit), a region-of-interest selecting unit 222 (a region-of-interest selecting unit), a size estimating unit 224 (a size estimating unit), the estimation state determining unit 226 (an estimation state determining unit), the reporting control unit 228 (a reporting control unit), the scope information acquiring unit 230 (a scope information acquiring unit, an individual information acquiring unit), an operation recognizing unit 232 (an operation recognizing unit), a recording control unit 234 (a recording control unit), and a display control unit 236 (a display control unit). Processing using these functions will be described below in detail.

The image processing unit 204 is capable of performing, with the above-described functions, calculation of a feature quantity of a medical image, processing of emphasizing or reducing a component of a specific frequency band, and processing of emphasizing or deemphasizing a specific target (a region of interest, blood vessels at a desired depth, or the like). The image processing unit 204 may include a special-light image acquiring unit that acquires a special-light image having information about a specific wavelength range on the basis of a normal-light image that is acquired by radiating light in the white range or light in a plurality of wavelength ranges as the light in the white range. In this case, a signal in the specific wavelength range can be acquired through computation based on color information of RGB (R: red, G: green, B: blue) or CMY (C: cyan, M: magenta, Y: yellow) included in the normal-light image. In addition, the image processing unit 204 may include a feature quantity image generating unit that generates a feature quantity image through computation based on at least one of a normal-light image that is acquired by radiating light in the white range or light in a plurality of wavelength ranges as the light in the white range or a special-light image that is acquired by radiating light in a specific wavelength range, and may acquire and display the feature quantity image as a medical image. The above-described processing is performed under control by the CPU 210.

Implementation of Functions by Various Types of Processors

The functions of the above-described units of the image processing unit 204 can be implemented by using various types of processors and a recording medium. The various types of processors include, for example, a central processing unit (CPU) which is a general-purpose processor that executes software (program) to implement various functions. Also, the various types of processors include a graphics processing unit (GPU) which is a processor dedicated to image processing, and a programmable logic device (PLD) which is a processor whose circuit configuration is changeable after manufacturing, such as a field programmable gate array (FPGA). In the case of performing learning and recognition of images as in the present invention, the configuration using a GPU is effective. Furthermore, the various types of processors include a dedicated electric circuit which is a processor having a circuit configuration designed exclusively for executing specific processing, such as an application specific integrated circuit (ASIC).

The function of each unit may be implemented by one processor or may be implemented by a plurality of processors of the same type or different types (for example, a combination of a plurality of FPGAs, a combination of a CPU and an FPGA, or a combination of a CPU and a GPU). A plurality of functions may be implemented by one processor. A first example of implementing a plurality of functions by one processor is that a combination of one or more CPUs and software constitute one processor and the one processor implements the plurality of functions, as represented by a computer. A second example is that a processor that implements the functions of an entire system by one integrated circuit (IC) chip is used, as represented by a system on chip (SoC). In this way, various functions are configured as a hardware structure by using one or more of the above-described various types of processors. Furthermore, the hardware structure of the various types of processors is, more specifically, electric circuitry formed by combining circuit elements such as semiconductor elements. The electric circuitry may be electric circuitry that implements the above-described functions by using logical disjunction, logical conjunction, logical negation, exclusive disjunction, and logical operation as a combination thereof.

When the above-described processor or electric circuitry executes the software (program), the code of the software to be executed that is readable by a computer (for example, the various types of processors or electric circuitry constituting the image processing unit 204, and/or a combination thereof) is stored in a non-transitory recording medium, such as a read only memory (ROM) 211, and the computer refers to the software. The software stored in the non-transitory recording medium includes a program for executing the medical image processing method (a method for operating a medical image processing apparatus) according to the present invention and data used in the execution (data related to acquisition of a medical image, data used for specifying a reporting condition and a reporting mode, parameters used in the size estimating unit, and so forth). The code may be recorded on a non-transitory recording medium, such as a magneto-optical recording device of various types or a semiconductor memory, instead of the ROM 211. In the processing using the software, a random access memory (RAM) 212 may be used as a transitory storage region, for example, and data stored in an electrically erasable and programmable read only memory (EEPROM) that is not illustrated can be referred to, for example. A recording unit 207 may be used as a "non-transitory recording medium".

The read only memory (ROM) 211 is a nonvolatile storage element (a non-transitory recording medium) and stores a computer-readable code of a program that causes the CPU 210 (a computer) and/or the image processing unit 204 (a computer) to execute various image processing methods (including the medical image processing method according to the present invention). The random access memory (RAM) 212 is a storage element for temporary storage in various processing operations and can be used as a buffer when acquiring an image. An audio processing unit 209 outputs a message (audio) about medical image processing, size estimation, reporting, or the like from a speaker 209A (a reporting unit, a reporting device, a speaker) under control by the CPU 210 and the image processing unit 204.

Operation Unit

The operation unit 208 can be constituted by devices such as a keyboard and a mouse that are not illustrated. A user is able to provide an instruction to execute medical image processing or designate a condition necessary for the execution (for example, setting of a reporting condition and a reporting mode described below) via the operation unit 208. An operation via the operation unit 208 includes setting of a reporting condition and a reporting mode (see FIGS. 6 and 7) and an operation of indicating that acquisition of a medical image of an area to be imaged has been ended. The above-described operation recognizing unit 232 recognizes a user operation performed via the operation unit 208. In accordance with the recognized operation, processing is performed by the CPU 210 and individual units of the image processing unit 204.

Information Stored in Recording Unit

Figure 4:
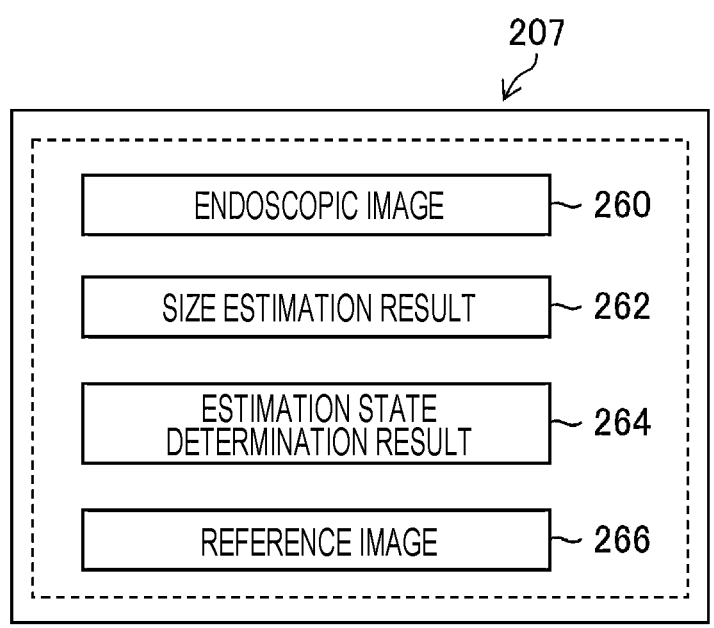
FIG. 4 is a diagram illustrating information stored in a recording unit.

As illustrated in FIG. 4, the recording unit 207 (a recording device, a storage device, a memory, a non-transitory recording medium) stores an endoscopic image 260 (an image, an endoscopic image, a medical image), a size estimation result 262 (a size estimation result), an estimation state determination result 264 (an estimation state determination result, an accuracy), a reference image 266 (a reference image; an image indicating an imaging state suitable for size estimation), and so forth. The reference image 266 is an image indicating an imaging state suitable for size estimation of a region of interest (an image in which a region of interest is seen such that size estimation can be accurately performed), and an image acquired in a past examination can be used. The reference image 266 is preferably stored in a database in association with an area, the type of region of interest, observation light, and other imaging conditions.

Individual Processes of Medical Image Processing Method

Figure 5:
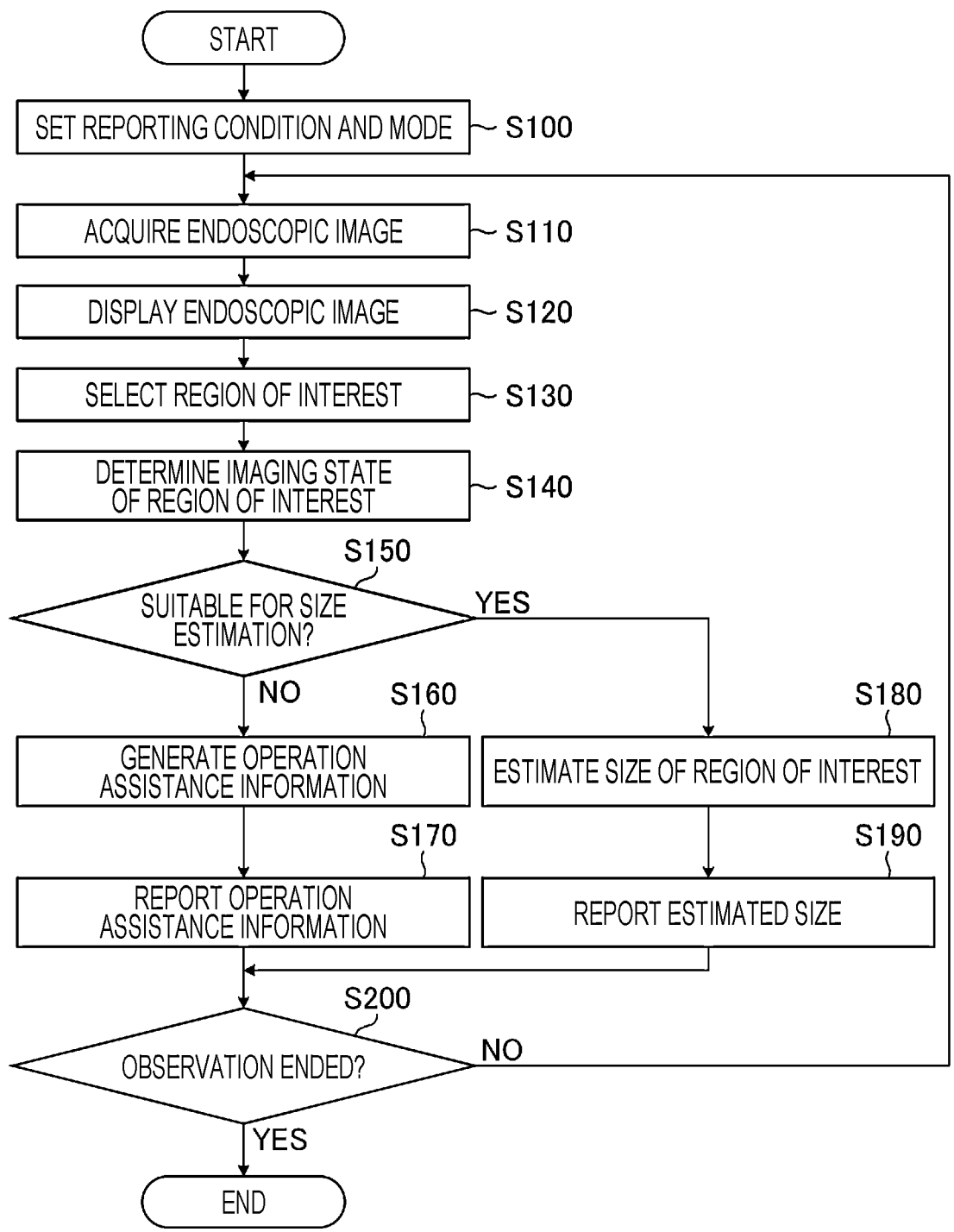
FIG. 5 is a flowchart illustrating a procedure of a medical image processing method according to the first embodiment.

FIG. 5 is a flowchart illustrating an overview of a process of a medical image processing method (a method for operating a medical image processing apparatus) according to the first embodiment.

Setting of Reporting Condition and Reporting Mode

The image processing unit 204 (the reporting control unit 228) sets a reporting condition and a reporting mode in accordance with a user operation performed via the operation unit 208 (step S100: a reporting condition setting step, a reporting mode setting step). The user is able to perform a setting operation via a screen 700 (displayed on the monitor 400) illustrated in FIG. 6.

The screen 700 has regions 702 to 712 in which radio buttons are disposed, and a region 714 in which a numerical value input field is disposed. The user is able to set whether to perform reporting (ON or OFF; the region 702) by operating a radio button. The user is also able to set "whether to perform reporting" (the region 702), "whether to report the accuracy of size estimation" (the region 704), "whether to perform reporting by screen display" (the region 706), and "whether to display a reference image" (the region 708) by operating radio buttons. Furthermore, the user is able to set "whether to superimpose and display operation assistance information on an endoscopic image (in a first region or a second region)" (the region 710) and "whether to perform reporting by audio output" (the region 712) by operating radio buttons. The "operation assistance information" is information for improving a result of the determination of "whether a region of interest in an endoscopic image is suitable for size estimation". The result of the determination can be improved by a user operation performed in accordance with the operation assistance information.

Furthermore, the user is able to set an "elapsed time from start to end of reporting (from start of a reporting state to switching to a non-reporting state)" by inputting a numerical value in the region 714. After the time (seconds) input to the region 714 has elapsed, the reporting control unit 228 switches reporting by the monitor 400 and/or the speaker 209A from a reporting state to a non-reporting state (stops or ends reporting). In the example in FIG. 6, the time from start to end of reporting is 2.0 seconds, but a different time may be set. The numerical value may be input by selecting a determined numerical value from a pull-down menu. With such switching to the non-reporting state, assistance can be finished according to necessity of the user, and excessive assistance can be suppressed. The reporting control unit 228 may decrease (reduce) a reporting intensity after the designated time has elapsed, in addition to or instead of ending reporting.

Figure 6:
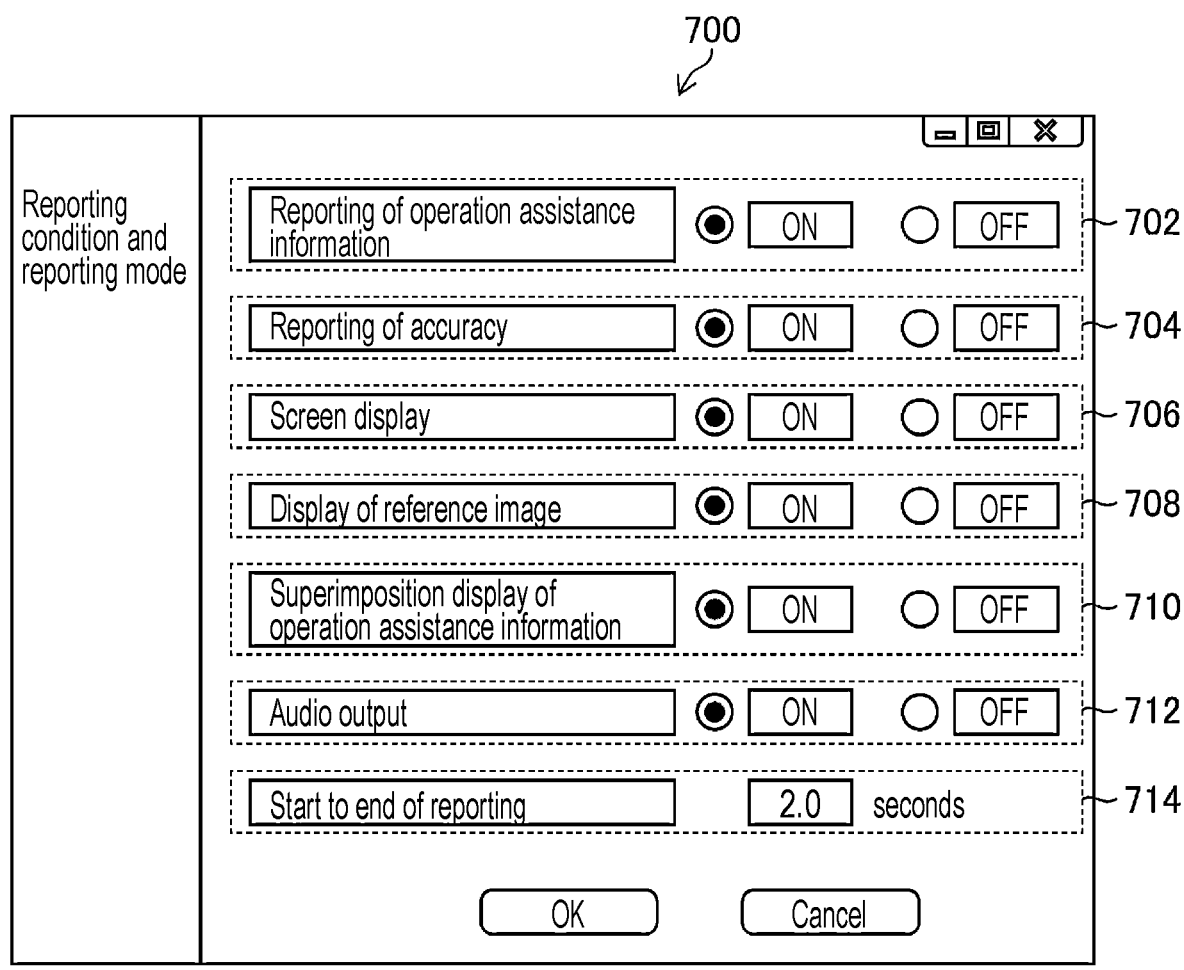
FIG. 6 is a diagram illustrating an example of a setting screen for a reporting condition and a reporting mode.
Figure 7:
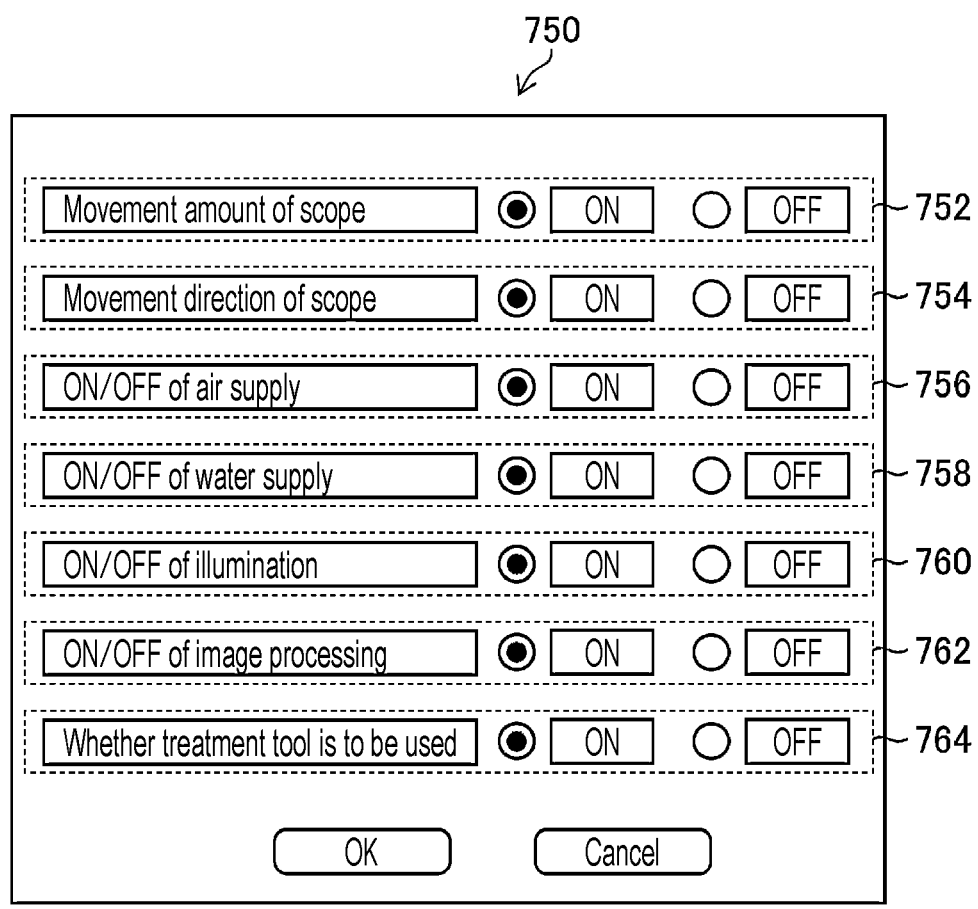
FIG. 7 is a diagram illustrating an example of a setting screen for operation assistance information.

Operation assistance information to be reported (first information to fifth information) may be set via a screen 750 illustrated in FIG. 7 in addition to the screen 700 in FIG. 6. On the screen 750 in FIG. 7, the user is able to set "whether to report an amount by which the endoscope 100 is to be moved" (a region 752; first information), "whether to report a direction in which the endoscope 100 is to be moved" (a region 754; first information), "whether to report that air supply is to be turned ON or OFF" (a region 756; second information), and "whether to report that water supply is to be turned ON or OFF" (a region 758; second information) by operating radio buttons. Furthermore, the user is able to set "whether to report that illumination is to be turned ON or OFF" (a region 760; third information), "whether to report that image processing is to be turned ON or OFF" (a region 762; fourth information), and "whether to report whether a treatment tool is to be used" (a region 764; fifth information) by operating radio buttons. Regarding air supply, water supply, illumination, and image processing, not only ON or OFF but also the degree may be allowed to be set via the screen.

The direction in which the endoscope 100 is to be moved and/or the amount by which the endoscope 100 is to be moved is "first information". ON/OFF (and the degree) of air supply and/or water supply is "second information". ON/OFF of illumination and/or the degree of illumination is "third information". ON/OFF of image processing on an acquired image and/or the degree thereof is "fourth information". Whether a treatment tool is to be used is "fifth information".

The user is able to change an imaging direction (imaging angle) or a distance by moving the endoscope 100 so that a region of interest is shot from the front or so that the region of interest becomes closer to a reference position (for example, the center). Air supply and/or water supply makes it possible to improve the clarity of a region including a region of interest, for example, by removing a residue or pigment. Illumination makes it possible to improve the brightness or clarity of an image and perform switching to observation light (normal light/special light, or the like) suitable for size estimation. Image processing makes it possible to, for example, remove unsharpness or a blur. By stopping use of a treatment tool (retracting a treatment tool into the tip rigid part 116) at a necessary timing, it is possible to prevent the treatment tool from overlapping a region of interest and interfering with size estimation. Reporting of such first information to fifth information based on the settings made by the user enables a region of interest to appear in an endoscopic image in a state suitable for size estimation.

In this way, in the endoscope system 10 (a medical image processing apparatus, an endoscope system), the user is able to set a reporting condition and a reporting mode according to necessity. The reporting control unit 228 is capable of performing appropriate reporting (assistance) in accordance with the settings. The above-described example is an example of settings, and another item (reporting by light or vibration or the like) may be set. The settings of a reporting condition and a reporting mode may be made not only at start of medical image processing but also at any timing during the processing. Furthermore, settings of a reporting condition and a reporting mode may be automatically made by the endoscope system 10 independently of a user operation.

Acquisition and Display of Endoscopic Image

The image acquiring unit 220 acquires an endoscopic image in time series (time-series image, a medical image) (step S110: an image acquisition step). The image acquiring unit 220 may acquire an endoscopic image captured by the endoscope 100, or may acquire the endoscopic image 260 stored in the recording unit 207. In a case where the image acquiring unit 220 acquires the endoscopic image captured by the endoscope 100, the recording control unit 234 is capable of recording (storing) the acquired image as the endoscopic image 260 in the recording unit 207.

The display control unit 236 causes the monitor 400 to display the acquired endoscopic image (step S120: an image display step).

Selection of Region of Interest

The region-of-interest selecting unit 222 selects a region of interest which is a target of size estimation in the acquired endoscopic image (step S130: a region-of-interest selection step). In a case where the endoscopic image has two or more regions of interest, the region-of-interest selecting unit 222 determines, in the image, one target on which size estimation is to be performed. For example, the region-of-interest selecting unit 222 may determine a region of interest having the largest area as a target, or may determine a region of interest having the highest accuracy of size estimation (described below regarding step S140) as a target. The region-of-interest selecting unit 222 may determine a target in accordance with a user operation performed via the operation unit 208.

To select a region of interest, the region-of-interest selecting unit 222 may detect the region of interest in an endoscopic image by using a neural network (not illustrated) such as a convolutional neural network (CNN). The CNN has, for example, an input layer, an intermediate layer, and an output layer. The intermediate layer calculates a feature quantity by convolutional operation or pooling processing. The output layer may include a fully connected layer, and outputs position information of a target (region of interest) on the basis of the feature quantity calculated by the intermediate layer. The region-of-interest selecting unit 222 may detect a region of interest by image processing other than a neural network.

Determination of Imaging State

The estimation state determining unit 226 determines the imaging state (the accuracy of size estimation) of the selected region of interest by, for example, image processing (step S140: an estimation state determination step). In a case where there are a plurality of regions of interest, the accuracy may be calculated for each of the plurality of regions of interest, and a region of interest may be selected on the basis of the result. In the case of estimating the size of a region of interest such as a lesion, the imaging state of the region of interest has a large influence, and it is difficult to accurately estimate the size in the following imaging states, for example. Thus, the accuracy is calculated in consideration of these circumstances.

As will be described below in detail, in the endoscope system 10, operation assistance information for improving the determination result (accuracy) is reported, and thereby the imaging state, position, and shape of a region of interest can be maintained in a state suitable for size estimation. This makes it possible to shorten endoscopy, reduce the burden, and ensure the consistency of an estimation result.

(1) Case Where Region Of Interest is Not Clearly Imaged

Figure 8A:
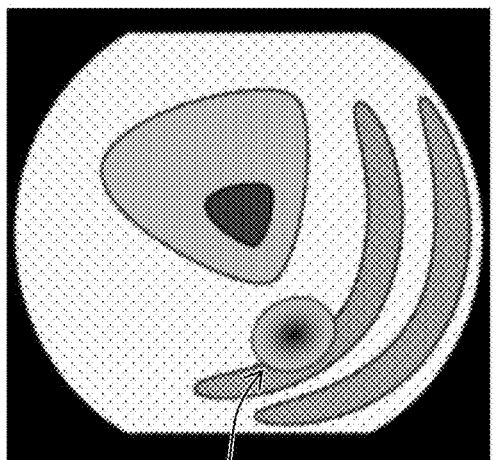
FIGS. 8A to 8D are diagrams illustrating examples of a state in which a region of interest is not clearly imaged.
Figure 8B:
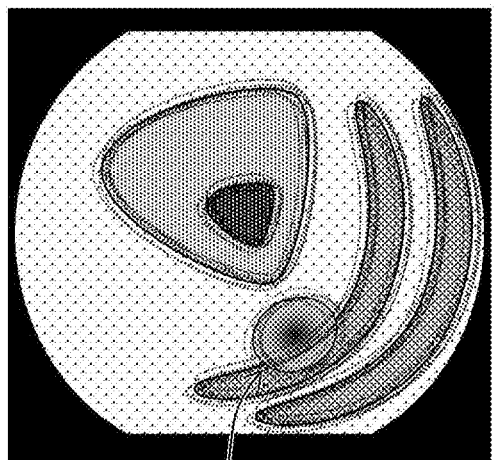
Figure 8C:
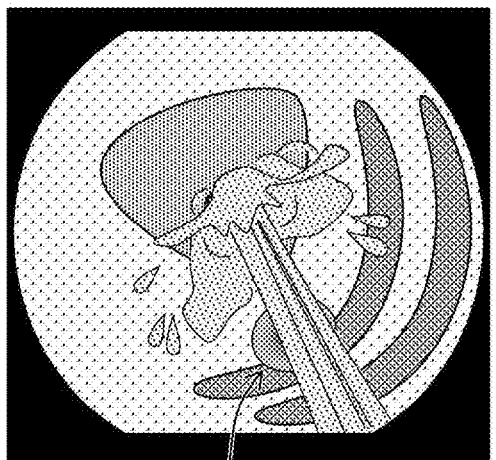
Figure 8D:
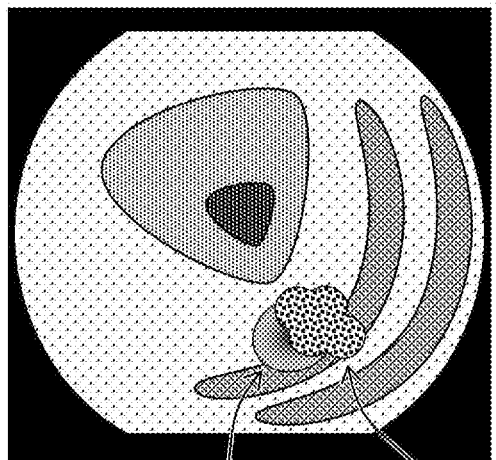

An endoscope is difficult to operate and requires skills to observe a lesion while fixing the endoscope. For this reason, defocus (unsharpness) and a motion blur (blur) as illustrated in FIG. 8A and FIG. 8B, respectively, may occur. Accordingly, the imaging state of a region of interest 802 may deteriorate, and the accuracy of size estimation may decrease. In the case of an endoscopic image, the region of interest 802 may be hidden by supplied water and a residue 804, as illustrated in FIG. 8C and FIG. 8D, respectively. Thus, the clarity of the imaging state can be reflected in an accuracy. The estimation state determining unit 226 is capable of performing, as "image processing" for calculating the accuracy described above, for example, obtaining of the clarity of an edge from a brightness signal and determining of defocus, or determining of a motion blur on the basis of the magnitude of a movement vector based on a comparison with a frame that is close in imaging timing. In addition, the estimation state determining unit 226 is capable of considering whether the air/water supply button 141 is to be operated, and a difference in color or brightness between a region of interest and a residue.

(2) Case Where Region of Interest is Not Seen at Appropriate Position

Figure 9A:
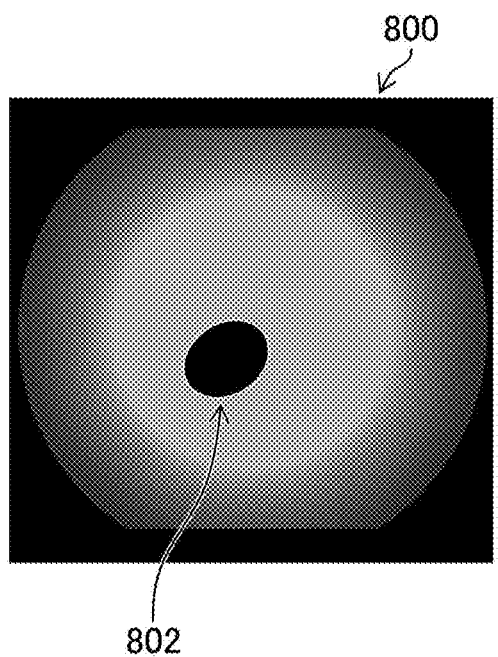
FIGS. 9A and 9B are diagrams illustrating an influence of the position of a region of interest on size estimation.
Figure 9B:
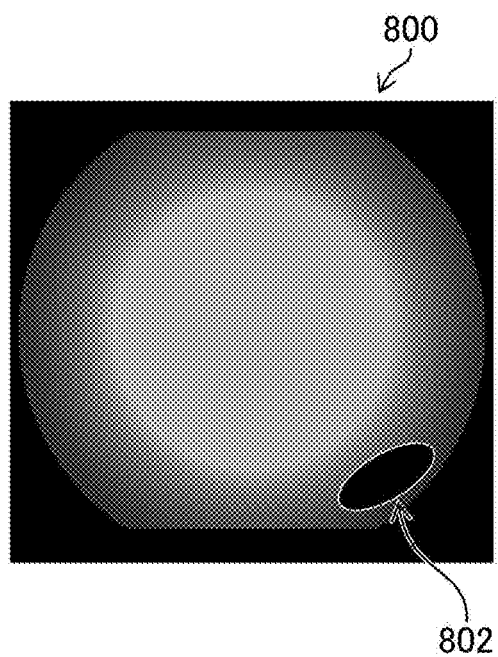

An endoscope has a wide angle of view, and an issue of aberration peculiar to an optical system occurs. For example, as illustrated in FIG. 9A, in a case where the region of interest 802 is near the center of an observation image 800, the distortion is small (in FIGS. 9A and 9B, the distortion is small in a light portion in gradation, and the distortion increases as the darkness increases). However, as illustrated in FIG. 9B, in a case where the region of interest 802 is near an edge of the observation image 800, the distortion is large and affects size estimation of the region of interest 802. Thus, the estimation state determining unit 226 is capable of reflecting the distance (the number of pixels) between a reference position in the image (for example, the center of the image) and the region of interest in the accuracy.

(3) Case where shape of region of interest in image is not appropriate

Figure 10A:
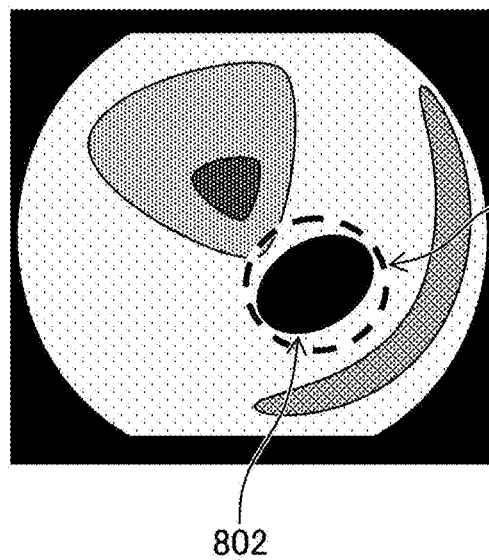
FIGS. 10A and 10B are diagrams illustrating an example in which the shape of a region of interest is determined on the basis of the circularity of the region of interest.
Figure 10B:
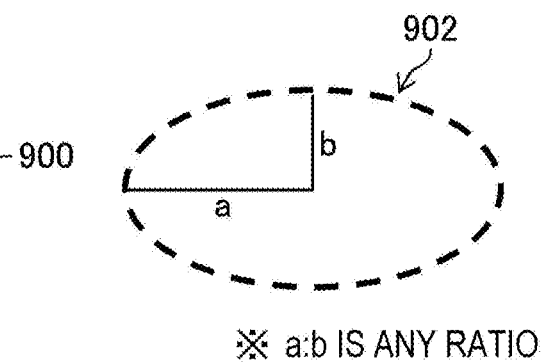

Tissues in a body, such as the large intestine and the stomach, are soft, and thus the shape of a region of interest constantly changes. In endoscopy, a region of interest is often found and observed in a tangential direction. However, in such a state, it may be impossible to determine the accurate size and shape of the region of interest. Thus, an imaging angle (for example, the angle formed by the normal direction of the region of interest and the optical axis direction of the imaging optical system 130), the degree of similarity with a predesignated figure (circle, ellipse, or the like), or the like can be reflected in the accuracy. FIGS. 10A and 10B illustrate an example in which the accuracy is determined on the basis of the circularity of the region of interest 802. FIG. 10A illustrates an example in which a circle 900 (perfect circle) serving as a criterion for determining the circularity is indicated by a broken line. As indicated by an ellipse 902 in FIG. 10B, the ratio between two axes may have any value (the figure serving as a determination criterion may either be a perfect circle or an ellipse). The ratio may be changed in accordance with the susceptibility of an imaged area or the like to change.

The accuracy may be represented by a continuous numerical value (for example, 0% to 100%), or may be represented by a discrete numerical value (an integer of 1 to 5, A to E, or the like). The recording control unit 234 is capable of recording the above-described accuracy as the estimation state determination result 264 in the recording unit 207.

The estimation state determining unit 226 determines, on the basis of the determination result (accuracy) in step S140, whether the region of interest is suitable for size estimation (step S150: an estimation state determination step). The estimation state determining unit 226 is capable of determining whether the region of interest is suitable for size estimation by comparing the calculated accuracy with a predetermined threshold value (for example, 70%, but is not limited to this value). The estimation state determining unit 226 may set the threshold value on the basis of a value input by a user. As a result of the determination in step S150, if the region of interest is suitable for size estimation (YES in step S150), the process proceeds to step S180, whereas if the region of interest is not suitable, the process proceeds to step S160.

Size Estimation of Region of Interest

The size estimating unit 224 estimates the size of the region of interest (step S180: a size estimation step). The "size" in the present invention is not a size on an image (the number of pixels) but a size in a real space (2 mm, 3 mm, or the like). Thus, it is possible to use a typical distance measurement technique (trigonometry or a time-of-flight method), such as measurement using parallax of multi-viewpoint imaging by a stereo camera, or measurement based on reflection or phase difference of laser, ultrasonic waves, or the like. In addition, because a study for accurately measuring a distance by using one camera has been conducted in recent years, distance measurement using deep learning may be used. In measurement using deep learning, an input is either a captured image or sensor signal information that can be acquired from the above-described device, or a combination thereof, an output is a size in a real space, and learning data is a size in a real space with high accuracy obtained by the above-described device or visual observation by an expert.

The size estimating unit 224 is also capable of performing estimation by comparison with an object whose size is known. As the "object whose size is known", for example, a "scale whose size is known and which is protruded from the forceps port 126 by a user operation" can be used. In accordance with the configuration of an endoscope or an imaging optical system, a scale using a laser beam as described in WO2018/159292A or JP2019-195643A may be used.

The reporting control unit 228 reports the estimation result by using the speaker 209A (a speaker, a reporting device) and/or the monitor 400 (a display, a reporting device) (step S190: a reporting step).

Generation and Display of Operation Assistance Information

If the determination result (accuracy) in step S140 is not suitable for size estimation, the reporting control unit 228 generates operation assistance information for improving the determination result of the estimation state (step S160: a generation step), and reports the operation assistance information by using the speaker 209A and/or the monitor 400 (step S170: a reporting step). The operation assistance information may indicate an operation to be performed on the endoscope 100 or may indicate a state suitable for size estimation. The operation assistance information may include at least one of the first information to the fifth information described above.

Reporting Mode 1

Figure 11A:
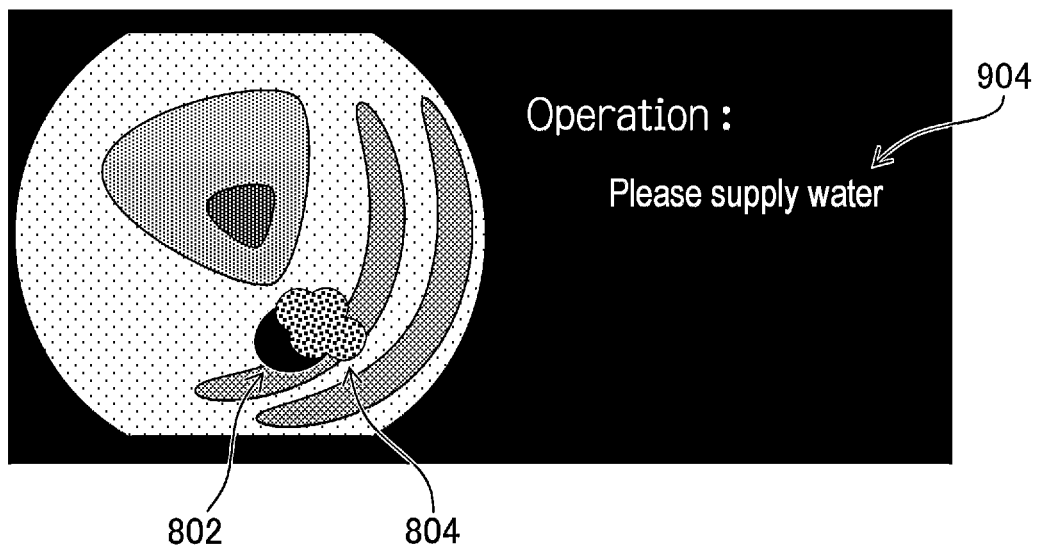
FIGS. 11A and 11B are diagrams illustrating examples of reporting operation assistance information.
Figure 11B:
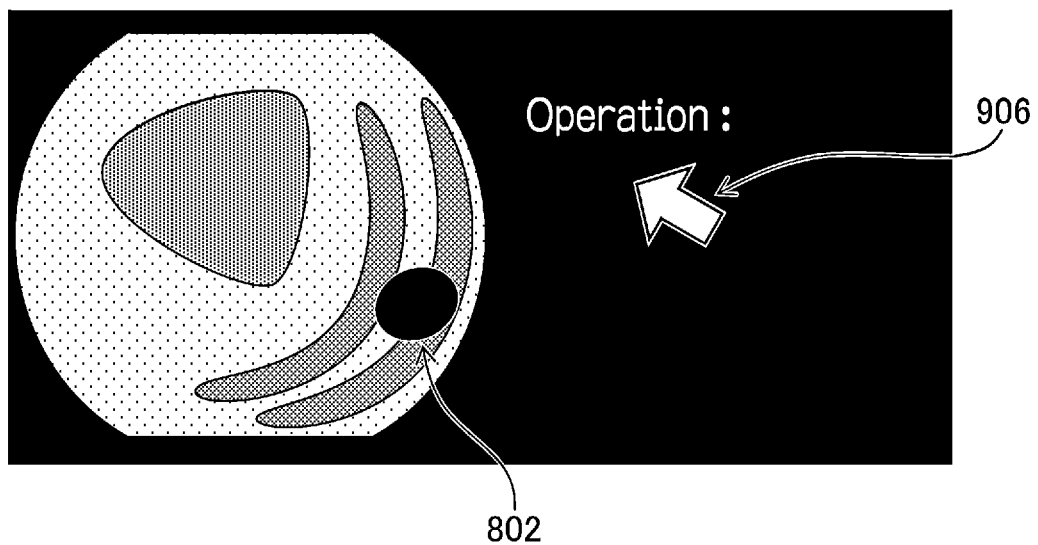

FIG. 11A illustrates an example in which a text message 904 "please supply water" (an operation on the endoscope 100; an example of second information) is displayed on the monitor 400 because the region of interest 802 is hidden by the residue 804 (the state illustrated in FIG. 8D), and FIG. 11B illustrates an example in which an arrow 906 (figure) indicating a direction in which the endoscope 100 is to be moved (an operation on the endoscope 100; an example of first information) is displayed because the region of interest is at an end of the field of view. These examples are examples in which display (reporting) is performed in the second region that does not overlap the endoscopic image. The reporting control unit 228 may display the operation assistance information on a screen different from that of the endoscopic image, or may display the operation assistance information on a monitor different from the monitor for displaying the endoscopic image. In addition, the reporting control unit 228 may report third to fifth information (operation assistance information regarding illumination, image processing, and use of a treatment tool) in accordance with the settings in step S100.

Figure 12A:
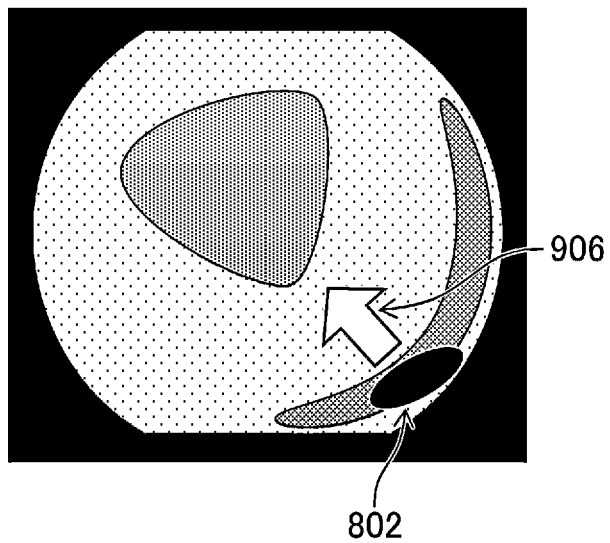
FIGS. 12A and 12B are other diagrams illustrating examples of reporting on an observation image.
Figure 12B:
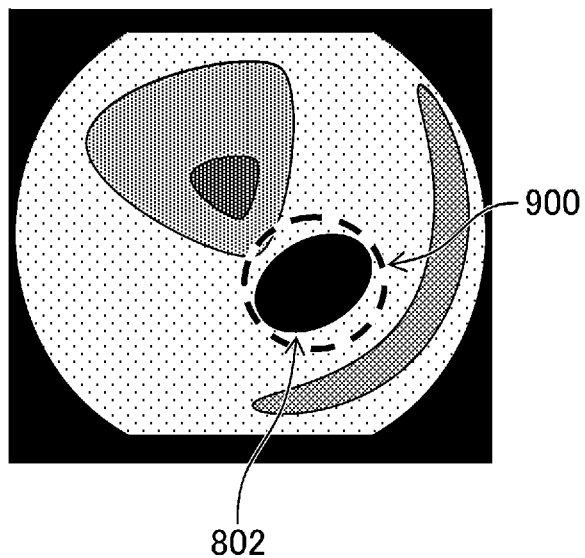

In the examples in FIGS. 11A and 11B, reporting is performed in a region (second region) that does not overlap the observation image. Alternatively, the reporting control unit 228 may perform reporting in a region (first region) in the observation image in accordance with the setting of the reporting condition (see the region 710 in FIG. 6). FIG. 12A illustrates an example in which the arrow 906 is displayed in an observation image, and FIG. 12B illustrates an example in which the circle 900 (figure) indicating the shape of a region of interest suitable for size estimation is superimposed and displayed on the observation image, and also a sound "please shoot from the front" is output from the speaker 209A.

Reporting Mode 2

Figure 13:
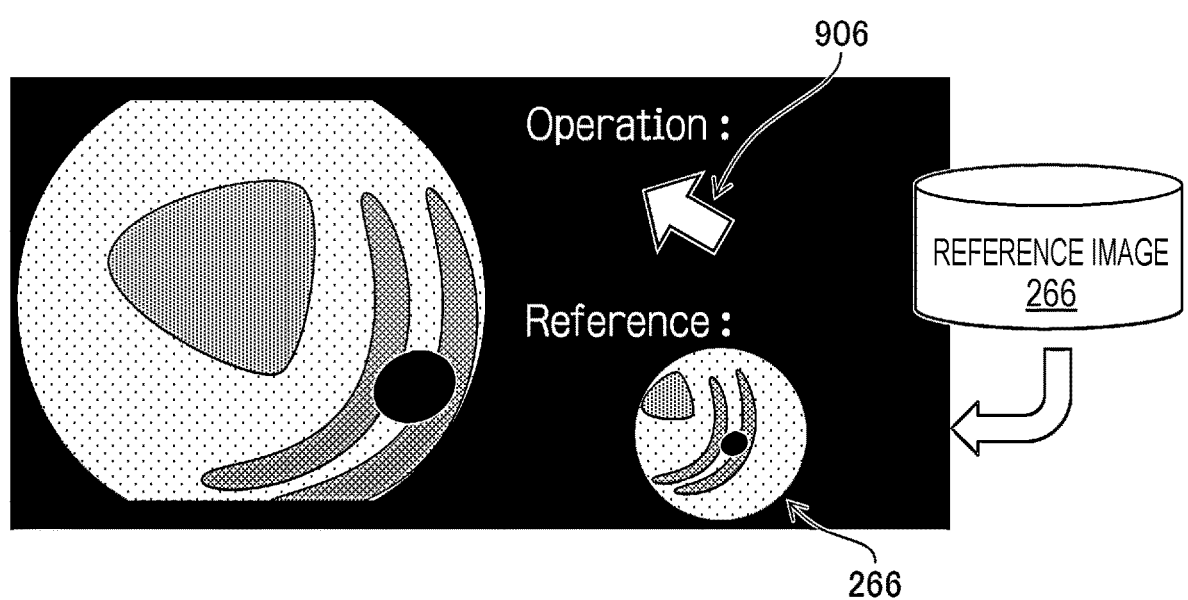
FIG. 13 is a diagram illustrating a display example of a reference image.

Depending on the situation of observation or examination, it may be unclear whether a user is able to sufficiently understand a state suitable for size estimation only by an operation instruction exemplified in the above-described "reporting mode 1". Thus, more specifically, a reference image of a state similar to a current image (an image indicating an imaging state suitable for size estimation; one aspect of operation assistance information) may be retrieved from a database (the reference image 266 stored in the recording unit 207), and the reference image may also be presented simultaneously, so as to increase the degree of understanding. The "state similar to a current image" is, for example, a state in which an imaged area is close, an imaging condition is similar, the type of region of interest is similar, or the state of the image is similar, to the current image, and specifically, a state in which an imaged area, the brightness or tint of the image, the wavelength of observation light, the size or shape of the region of interest, the type of endoscope, an imaging date and time, or the like is similar. FIG. 13 is a diagram illustrating an example in which the reporting control unit 228 displays the arrow 906 indicating an operation direction of the endoscope 100 and the reference image 266 (an image in which a region of interest is clearly seen near the center of the image) in the second region.

Reporting Mode 3

Figure 14A:
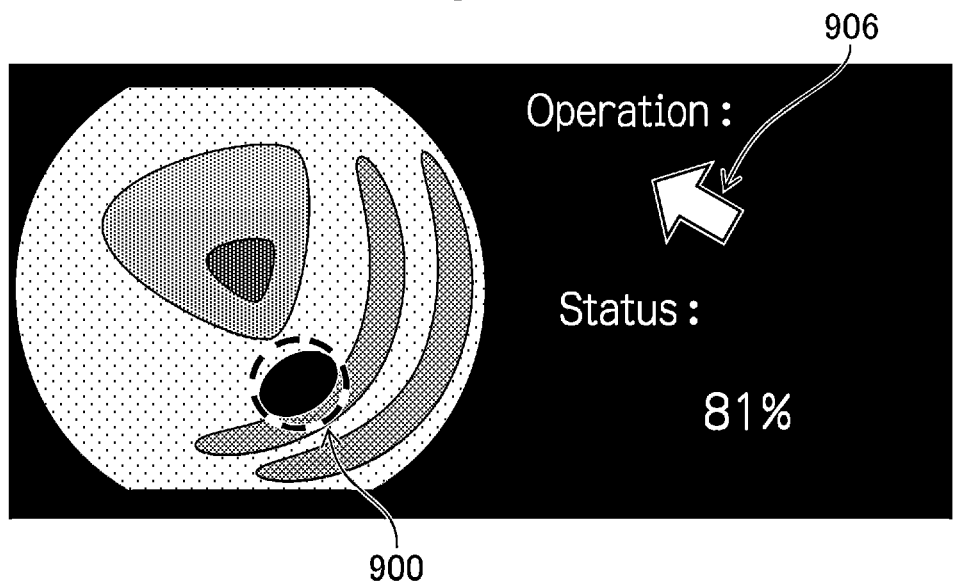
FIGS. 14A and 14B are diagrams illustrating examples of reporting an accuracy.
Figure 14B:
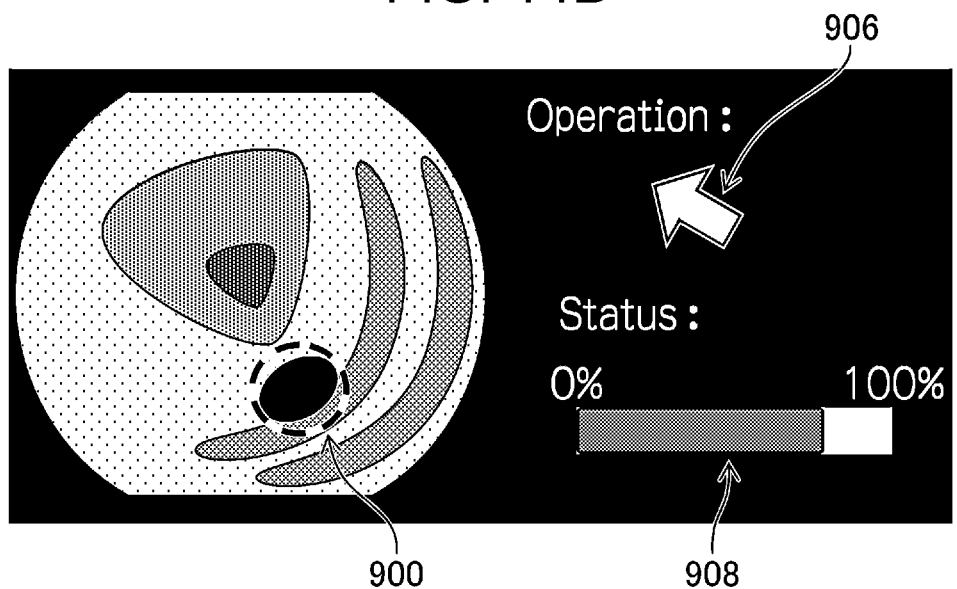

The above-described "reporting modes 1 and 2" are examples of reporting operation assistance information alone. By simultaneously reporting the accuracy of size estimation and imaging state information (for example, image clarity, presence or absence and the degree of unsharpness or blur, presence or absence of water supply or residue, usage state of a treatment tool, or the like), it is possible to easily grasp how the endoscope system 10 recognizes a region of interest and an adjustment state in the case of following the operation assistance information. FIG. 14A is a diagram illustrating a state in which an accuracy (in this case, 81%) is displayed as a numerical value in addition to the arrow 906 indicating an operation direction of the endoscope 100 and the circle 900. FIG. 14B is a diagram illustrating a state in which an accuracy is displayed as a bar-shaped figure 908 (the length of the colored portion indicates the accuracy, where the left end corresponds to 0% and the right end corresponds to 100%) in the second region. The reporting control unit 228 may output an accuracy and imaging state information by using a sound.

Reporting Mode 4

Figure 15A:
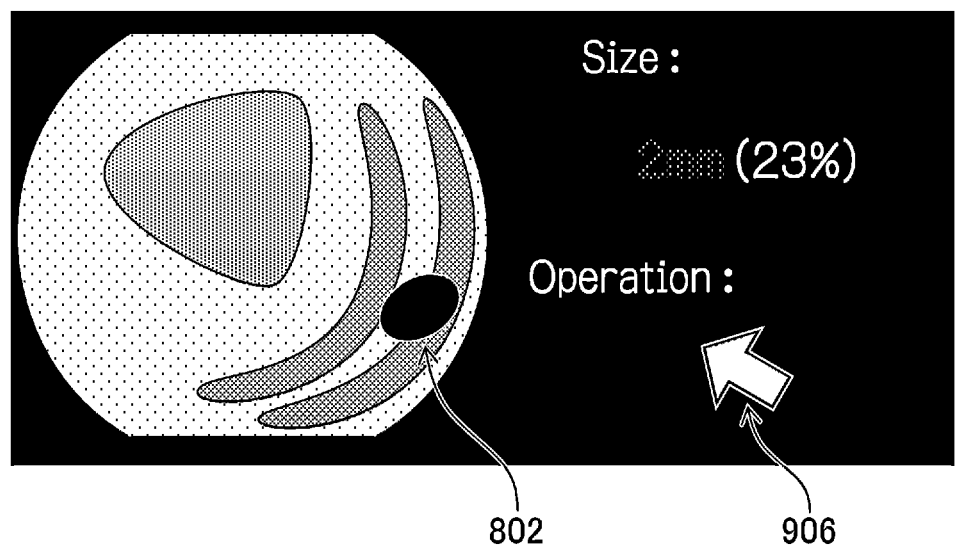
FIGS. 15A and 15B are diagrams illustrating examples of reporting size information and operation assistance information in combination.
Figure 15B:
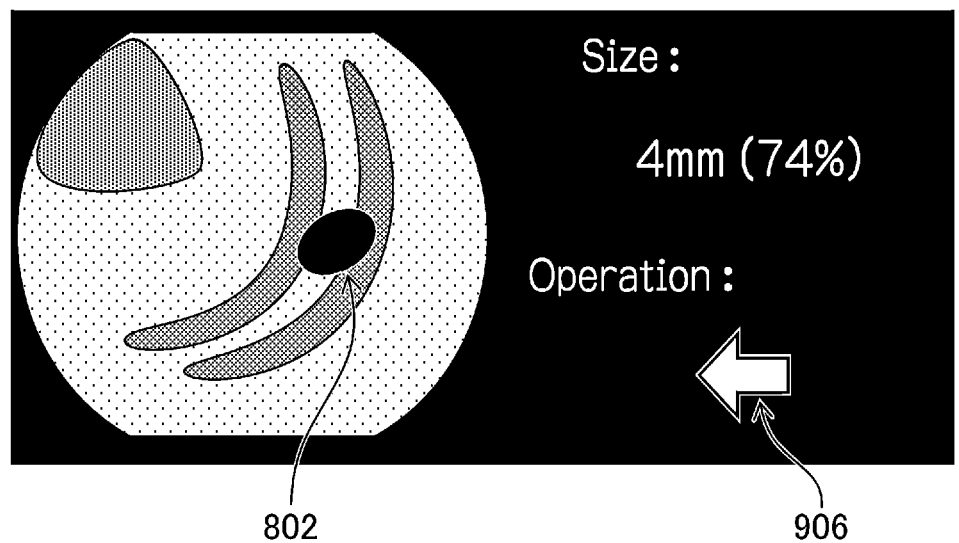

FIGS. 15A and 15B are diagrams illustrating a state in which a size estimation result and an accuracy are reported in addition to operation assistance information. In the example illustrated in FIG. 15A, the accuracy of size estimation is low (23%), and thus the estimated size (2 mm) is displayed in a dark color. In the example illustrated in FIG. 15B, the accuracy of size estimation is high (74%), and thus the estimated size (4 mm) is clearly displayed in a white color. In this way, the reporting control unit 228 may change the mode of reporting depending on whether the accuracy is low or high.

Recognition of User Operation and Reporting of Determination Result

Figure 16:
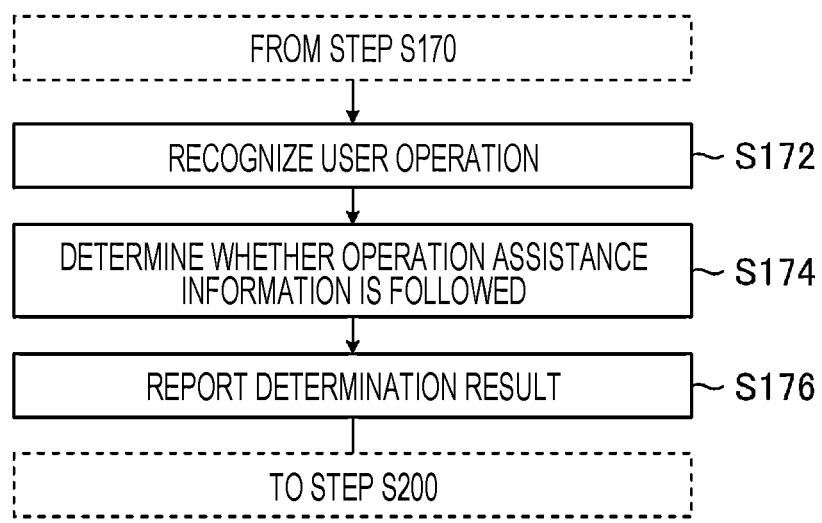
FIG. 16 is a flowchart illustrating a process of recognizing a user operation and reporting a determination result.

There is a possibility that a user is unable to instantaneously understand the content of operation assistance information depending on the reporting mode of the operation assistance information. Thus, the endoscope system 10 may determine whether the user is performing an operation in accordance with the operation assistance information and report the determination. For example, as illustrated in the flowchart in FIG. 16, the operation recognizing unit 232 (see FIG. 3) recognizes a user operation for operation assistance information (step S172: an operation recognition step) and determines whether the recognized user operation follows the operation assistance information (step S174: a determination step), and the reporting control unit 228 reports the determination result by using the monitor 400 and/or the speaker 209A (step S176: a reporting step).

Figure 17A:
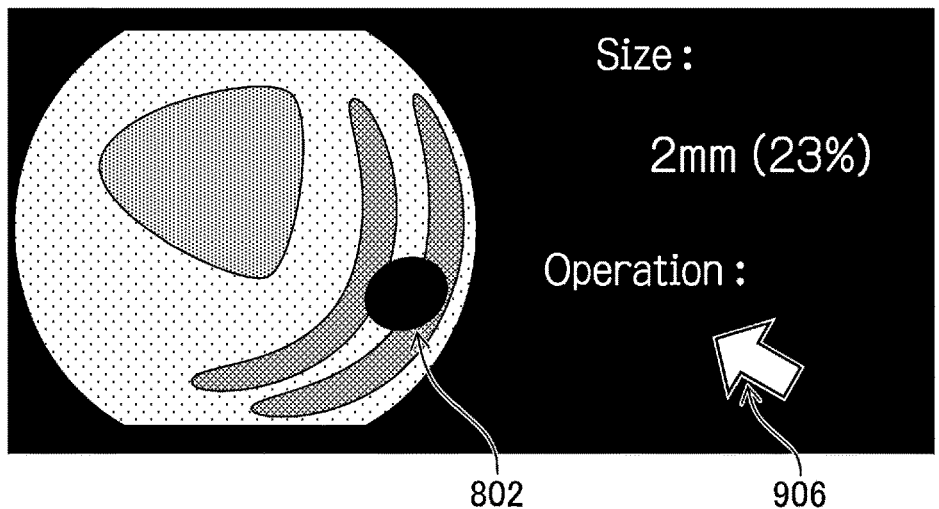
FIGS. 17A to 17C are diagrams illustrating examples of reporting on an observation image.
Figure 17B:
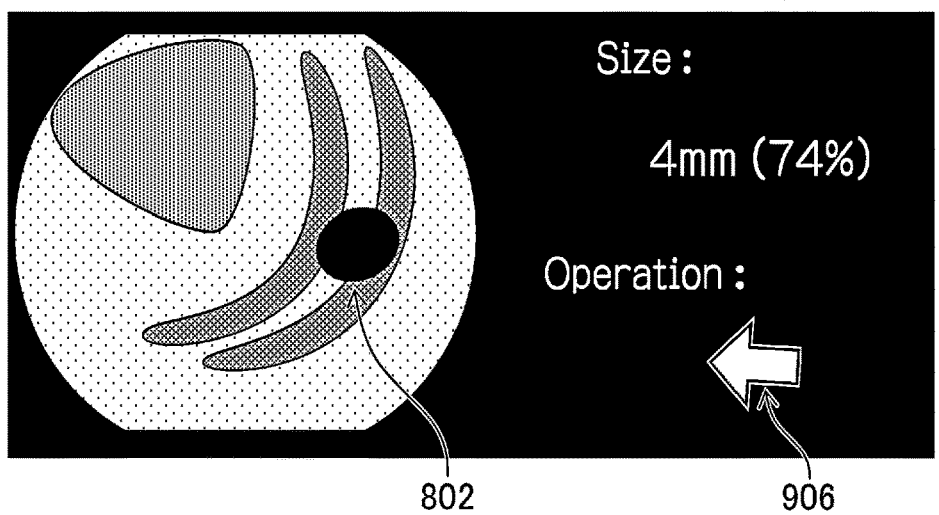
Figure 17C:
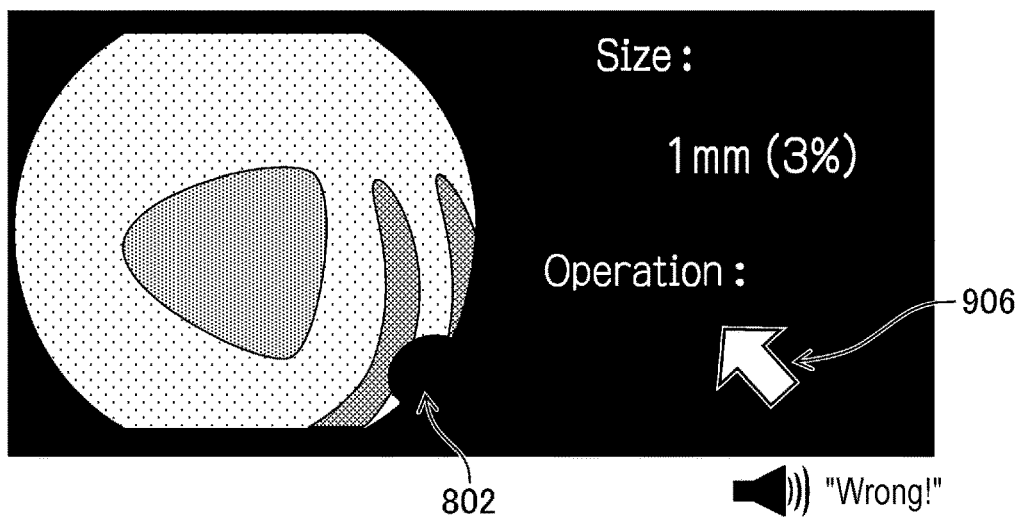

FIGS. 17A to 17C are diagrams illustrating examples of reporting of a determination result for a user operation. FIG. 17A illustrates a state before the user performs an operation (a state in which operation assistance information has been reported). In this state, the accuracy of the size estimation result is low (23%), and the user needs to locate the region of interest near the center of the endoscopic image by moving the endoscope 100 forward or backward or causing the endoscope 100 to bend in accordance with the arrow 906 (one aspect of operation assistance information). FIG. 17B illustrates an example of a reporting state after the user has performed an operation. Compared with FIG. 17A, the position of the region of interest is close to the center (reference position). Thus, the operation recognizing unit 232 determines that "the user operation follows the operation assistance information", and the reporting control unit 228 outputs a sound "Right!" (a determination result) from the speaker 209A. FIG. 17C illustrates an example of a reporting state after the user has performed an operation. In this example, compared with FIG. 17A, the position of the region of interest is not close to the center (the accuracy decreases). Thus, the operation recognizing unit 232 determines that "the user operation does not follow the operation assistance information", and the reporting control unit 228 outputs a sound "Wrong!" (a determination result) from the speaker 209A. With such reporting, the user is able to easily grasp whether his/her operation corresponds to the operation assistance information, and the user can be assisted so that the size of the region of interest can be accurately estimated.

In the flowchart in FIG. 5, a size estimation result is reported if the region of interest is suitable for size estimation (YES in step S150), but the reporting control unit 228 may report the estimation result also if the region of interest is unsuitable for size estimation (NO in step S150).

The CPU 210 and the image processing unit 204 repeat the process of steps S110 to S190 until observation ends (during NO in step S200).

As described above, in the medical image processing apparatus, endoscope system, medical image processing method, and program according to the present invention, it is possible to assist a user in accurately estimating the size of a region of interest.

Appendices

In addition to the above-described embodiment and examples, the configurations described below are included in the scope of the present invention.

Appendix 1

A medical image processing apparatus wherein
a medical image analysis processing unit detects a region of interest on the basis of a feature quantity of pixels of a medical image, the region of interest being a region to be focused on, and
a medical image analysis result acquiring unit acquires an analysis result of the medical image analysis processing unit.

Appendix 2

A medical image processing apparatus wherein
a medical image analysis processing unit detects presence or absence of a target to be focused on, on the basis of a feature quantity of pixels of a medical image, and
a medical image analysis result acquiring unit acquires an analysis result of the medical image analysis processing unit.

Appendix 3

The medical image processing apparatus wherein
the medical image analysis result acquiring unit
acquires the analysis result of the medical image from a recording device in which the analysis result is recorded, and
the analysis result is either or both of the region of interest which is a region to be focused on included in the medical image and the presence or absence of the target to be focused on.

Appendix 4

The medical image processing apparatus wherein the medical image is a normal-light image acquired by radiating light in a white range or light in a plurality of wavelength ranges as the light in the white range.

Appendix 5

The medical image processing apparatus wherein
the medical image is an image acquired by radiating light in a specific wavelength range, and
the specific wavelength range is a range narrower than a white wavelength range.

Appendix 6

The medical image processing apparatus wherein the specific wavelength range is a blue or green range in a visible range.

Appendix 7

The medical image processing apparatus wherein the specific wavelength range includes a wavelength range of 390 nm or more and 450 nm or less or a wavelength range of 530 nm or more and 550 nm or less, and the light in the specific wavelength range has a peak wavelength in the wavelength range of 390 nm or more and 450 nm or less or the wavelength range of 530 nm or more and 550 nm or less.

Appendix 8

The medical image processing apparatus wherein the specific wavelength range is a red range in a visible range.

Appendix 9

The medical image processing apparatus wherein the specific wavelength range includes a wavelength range of 585 nm or more and 615 nm or less or a wavelength range of 610 nm or more and 730 nm or less, and the light in the specific wavelength range has a peak wavelength in the wavelength range of 585 nm or more and 615 nm or less or the wavelength range of 610 nm or more and 730 nm or less.

Appendix 10

The medical image processing apparatus wherein the specific wavelength range includes a wavelength range in which a light absorption coefficient is different between oxyhemoglobin and deoxyhemoglobin, and the light in the specific wavelength range has a peak wavelength in the wavelength range in which the light absorption coefficient is different between oxyhemoglobin and deoxyhemoglobin.

Appendix 11

The medical image processing apparatus wherein the specific wavelength range includes a wavelength range of 400±10 nm, a wavelength range of 440±10 nm, a wavelength range of 470±10 nm, or a wavelength range of 600 nm or more and 750 nm or less, and the light in the specific wavelength range has a peak wavelength in the wavelength range of 400±10 nm, the wavelength range of 440±10 nm, the wavelength range of 470±10 nm, or the wavelength range of 600 nm or more and 750 nm or less.

Appendix 12

The medical image processing apparatus wherein
the medical image is an inside-of-living-body image depicting an inside of a living body, and
the inside-of-living-body image has information about fluorescence emitted by a fluorescent substance in the living body.

Appendix 13

The medical image processing apparatus wherein the fluorescence is acquired by irradiating the inside of the living body with excitation light whose peak is 390 nm or more and 470 nm or less.

Appendix 14

The medical image processing apparatus wherein
the medical image is an inside-of-living-body image depicting an inside of a living body, and
the specific wavelength range is a wavelength range of infrared light.

Appendix 15

The medical image processing apparatus wherein the specific wavelength range includes a wavelength range of 790 nm or more and 820 nm or less or a wavelength range of 905 nm or more and 970 nm or less, and the light in the specific wavelength range has a peak wavelength in the wavelength range of 790 nm or more and 820 nm or less or the wavelength range of 905 nm or more and 970 nm or less.

Appendix 16

The medical image processing apparatus wherein
a medical image acquiring unit includes a special-light image acquiring unit that acquires a special-light image having information about the specific wavelength range on the basis of a normal-light image that is acquired by radiating light in a white range or light in a plurality of wavelength ranges as the light in the white range, and
the medical image is the special-light image.

Appendix 17

The medical image processing apparatus wherein a signal in the specific wavelength range is acquired through computation based on color information of RGB or CMY included in the normal-light image.

Appendix 18

The medical image processing apparatus including
a feature quantity image generating unit that generates a feature quantity image through computation based on at least one of a normal-light image or a special-light image, the normal-light image being acquired by radiating light in a white range or light in a plurality of wavelength ranges as the light in the white range, the special-light image being acquired by radiating light in a specific wavelength range, wherein
the medical image is the feature quantity image.

Appendix 19

An endoscope apparatus including:
the medical image processing apparatus according to any one of appendices 1 to 18; and
an endoscope that acquires an image by radiating at least any one of light in a white wavelength range or light in a specific wavelength range.

Appendix 20

A diagnosis assistance apparatus including the medical image processing apparatus according to any one of appendices 1 to 18.

Appendix 21

A medical work assistance apparatus including the medical image processing apparatus according to any one of appendices 1 to 18.

The embodiment of the present invention and other examples have been described above. The present invention is not limited to the above-described aspects and various modifications can be made without deviating from the spirit of the present invention.

REFERENCE SIGNS LIST 10 endoscope system
100 endoscope
102 handheld operation section
104 insertion section
106 universal cable
108 light guide connector
112 soft part
114 bending part
116 tip rigid part
116A distal-end-side surface
123 illumination unit
123A illumination lens
123B illumination lens
126 forceps port
130 imaging optical system
132 imaging lens
134 imaging element
136 driving circuit
138 AFE
139 scope information recording unit
141 air/water supply button
142 suction button
143 function button
144 imaging button
170 light guide
200 processor
202 image input controller
204 image processing unit 205 communication control unit
206 video output unit
207 recording unit
208 operation unit
209 audio processing unit
209A speaker
210 CPU
211 ROM
212 RAM
220 image acquiring unit
222 region-of-interest selecting unit
224 size estimating unit
226 estimation state determining unit
228 reporting control unit
230 scope information acquiring unit
232 operation recognizing unit
234 recording control unit
236 display control unit
260 endoscopic image
262 size estimation result
264 estimation state determination result
266 reference image
300 light source apparatus
310 light source
310B blue light source
310G green light source
310R red light source
310V violet light source
330 diaphragm
340 condenser lens
350 light source control unit
400 monitor
700 screen
702 region
704 region
706 region
708 region
710 region
712 region
714 region
750 screen
752 region
754 region
756 region
758 region
760 region
762 region
764 region
800 observation image
802 region of interest
804 residue
900 circle
902 ellipse
906 arrow
908 figure
S100-S200 individual steps of medical image processing method

What is claimed is:

1. An endoscope system comprising:
an endoscope having an insertion section; and
one or more processors,
the one or more processors being configured to:
acquire a plurality of images captured sequentially, wherein the plurality of images are obtained from an image sensor disposed at a distal end of the insertion section of the endoscope;
display the plurality of images sequentially on a display;
detect a lesion in each of the plurality of images;
estimate a size of the lesion in response to the lesion having been detected in any of the plurality of images, wherein the one or more processors are further configured to:
determine whether the lesion is suitable for size estimation according to a clarity of an area containing the lesion in one of the plurality of images in which the lesion has been detected, a position of the lesion in the one of the plurality of images in which the lesion has been detected, and a shape of the lesion in the one of the plurality of images in which the lesion has been detected;
display the size of the lesion on the display in a case where the one or more processors have determined that the lesion is suitable for size estimation; and
display an operation assistance information in a case where the one or more processors have determined that the lesion is not suitable size estimation, wherein the operation assistance information is displayed on the display to guide a user to improve at least one of the clarity of the area containing the lesion in one of the plurality of images in which the lesion has been detected, the position of the lesion in the one of the plurality of images in which the lesion has been detected, or the shape of the lesion in the one of the plurality of images in which the lesion has been detected.

2. The medical image processing apparatus according to claim 1, wherein the one or more processors is configured to calculate, by image processing, an accuracy of the size estimation and compare the accuracy with a predetermined threshold value, thereby determining whether the region of interest is suitable for the size estimation.

3. The medical image processing apparatus according to claim 2, wherein the one or more processors is configured to report the accuracy by using a reporting device.

4. The medical image processing apparatus according to claim 2, wherein the one or more processors is configured to calculate the accuracy by using the clarity of the area including the region of interest.

5. The medical image processing apparatus according to claim 2, wherein the one or more processors is configured to calculate the accuracy in accordance with a distance between a reference position and the region of interest in the acquired images.

6. The medical image processing apparatus according to claim 2, wherein the one or more processors is configured to calculate the accuracy in accordance with an imaging angle for imaging the region of interest.

7. The medical image processing apparatus according to claim 1, comprising
a storage device configured to store one or more reference images each indicating an imaging state suitable for the size estimation, wherein
the one or more processors is configured to cause a reporting device to display one or more reference images.

8. The medical image processing apparatus according to claim 1, wherein the one or more processors is configured to cause a reporting device to display a result of whether the lesion is suitable for the size estimation and the operation assistance information in a first region in the plurality of images and/or a second region that does not overlap the plurality of images.

9. The medical image processing apparatus according to claim 1, wherein the one or more processors is configured to determine, in an image of the plurality of images having two or more regions of interest, one target on which the size estimation is to be performed.

10. The medical image processing apparatus according to claim 9, wherein the one or more processors is configured to determine, as the target, a region of interest having a largest area of the two or more regions of interest.

11. The medical image processing apparatus according to claim 9, wherein the one or more processors is configured to determine, as the target, a region of interest having a highest accuracy of the size estimation of the two or more regions of interest.

12. The medical image processing apparatus according to claim 1, wherein the one or more processors is configured to perform the size estimation on the region of interest, and report, by using a reporting device, a result of the size estimation.

13. The medical image processing apparatus according to claim 1, wherein the one or more processors is configured to recognize a user operation, make a determination of whether the recognized user operation follows the operation assistance information, and report, by using a reporting device, a result of the size determination.

14. An endoscope system comprising:
the medical image processing apparatus according to claim 1;
a reporting device; and
an endoscope configured to be inserted into a subject as a photographic subject and capture the plurality of images, wherein
the one or more processors is configured to acquire the plurality of images captured by the endoscope.

15. The endoscope system according to claim 14, wherein
the reporting device comprises a display configured to perform a screen display of information and a speaker configured to output a sound, and
the one or more processors is configured to report, by using the display and the speaker, a result of whether the lesion is suitable for the size estimation and the operation assistance information with use of at least one of a figure, text, or a sound.

16. The endoscope system according to claim 14, wherein the operation assistance information includes at least one of first information indicating a direction in which the endoscope is to be moved or an amount by which the endoscope is to be moved, second information indicating ON or OFF of air supply from the endoscope or ON or OFF of water supply from the endoscope, third information indicating ON or OFF of illumination from the endoscope or a degree of the illumination, fourth information indicating ON or OFF of image processing on the acquired images or a degree of the image processing, or fifth information indicating whether a treatment tool is to be used.

17. The endoscope system according to claim 14, wherein the one or more processors is configured to
acquire individual information of the endoscope, and
perform a determination of whether the lesion is suitable for the size estimation and a reporting on a basis of an individual information.

18. A medical image processing method performed by one or more processors and an insertion section of an endoscope system, the method comprising:
acquiring a plurality of images captured sequentially, wherein the plurality of images are obtained from an image sensor disposed at a distal end of the insertion section of the endoscope;
displaying the plurality of images sequentially on a display;
detecting a lesion in each of the plurality of images;
estimating a size of the lesion in response to the lesion having been detected in any of the plurality of images, wherein estimating the size of the lesion comprising:
determining whether the lesion is suitable for size estimation according to a clarity of an area containing the lesion in one of the plurality of images in which the lesion has been detected, a position of the lesion in the one of the plurality of images in which the lesion has been detected, and a shape of the lesion in the one of the plurality of images in which the lesion has been detected;
displaying the size of the lesion on the display in a case where the one or more processors have determined that the lesion is suitable for size estimation; and
displaying an operation assistance information in a case where the one or more processors have determined that the lesion is not suitable size estimation, wherein the operation assistance information is displayed on the display to guide a user to improve at least one of the clarity of the area containing the lesion in one of the plurality of images in which the lesion has been detected, the position of the lesion in the one of the plurality of images in which the lesion has been detected, or the shape of the lesion in the one of the plurality of images in which the lesion has been detected.

19. A non-transitory, computer-readable tangible recording medium storing a program which causes, when read by the one or more processors of the medical image processing apparatus, the one or more processors to perform the medical image processing method according to claim 18.

20. The medical image processing apparatus of claim 1, wherein when the one or more processors have determined that the lesion is not suitable for size estimation, display operation assistance information on the display.

* * * * *